US012758279B2

(12) United States Patent
Moses et al.

(10) Patent No.: US 12,758,279 B2
(45) Date of Patent: Oct. 13, 2026

(54) PIEZOELECTRIC ORTHOPEDIC IMPLANT AND METHODOLOGY

(71) Applicant: Spark Assets LLC, Needham, MA (US)

(72) Inventors: Ziev Moses, Needham, MA (US); Kevin Chappuis, Saugus, MA (US); Luke Diehl, Medford, MA (US); Lance Smith, Edmond, OK (US)

(73) Assignee: Spark Assets LLC, Needham, MA (US)

(*) Notice: Subject to any disclaimer, the term of this patent is extended or adjusted under 35 U.S.C. 154(b) by 310 days.

(21) Appl. No.: 18/308,455

(22) Filed: Apr. 27, 2023

(65) Prior Publication Data

US 2023/0346437 A1 Nov. 2, 2023

Related U.S. Application Data

(60) Provisional application No. 63/396,019, filed on Aug. 8, 2022, provisional application No. 63/335,343, filed on Apr. 27, 2022.

(51) Int. Cl.
*A61B 17/80* (2006.01)

(52) U.S. Cl.
CPC ................................ *A61B 17/8047* (2013.01)

(58) Field of Classification Search
CPC . A61B 17/80; A61B 17/8004; A61B 17/8014; A61B 17/8033; A61B 17/8042; A61B 17/8047; A61B 17/8052; A61B 17/8057; A61B 17/86; A61B 17/8605; A61B 17/861; A61B 17/8615; A61B 17/8625; A61B 17/863; A61B 17/8635;
(Continued)

(56) References Cited

U.S. PATENT DOCUMENTS

| | | | | | |
|---|---|---|---|---|---|
| 5,057,111 | A * | 10/1991 | Park | A61B 17/8047 606/70 |
| 5,797,912 | A * | 8/1998 | Runciman | A61B 17/8047 606/301 |

(Continued)

FOREIGN PATENT DOCUMENTS

| | | | | |
|---|---|---|---|---|
| CN | 114401684 A * | 4/2022 | A61N 1/04 |
| CN | 116473649 A * | 7/2023 | A61B 17/80 |

(Continued)

OTHER PUBLICATIONS

United States Patent and Trademark Office, International Search Report and the Written Opinion of the International Searching Authority, or the Declaration, issued in International Patent Application No. PCT/US2023/020201, dated Jul. 21, 2023, 18 pages.

(Continued)

*Primary Examiner* — Eric S Gibson
(74) *Attorney, Agent, or Firm* — Greenberg Traurig, LLP

(57) ABSTRACT

An orthopedic implant assembly includes a bone plate configured to couple the implant assembly to a fractured bone. A piezoelectric component is disposed on the bone plate and configured to produce an electrical output corresponding to a load the piezoelectric component is subjected to. When the implant is in contact with the fractured bone the electrical output is transmitted to the fractured bone.

25 Claims, 27 Drawing Sheets

(58) Field of Classification Search
CPC ................ A61B 17/864; A61B 17/866; A61B 2017/0011
See application file for complete search history.

(56) References Cited

U.S. PATENT DOCUMENTS

| | | | | |
|---|---|---|---|---|
| 6,034,296 | A * | 3/2000 | Elvin | A61B 5/0031 128/903 |
| 6,290,724 | B1 | 9/2001 | Marino | |
| 7,431,734 | B2 * | 10/2008 | Danoff | A61F 2/30721 607/51 |
| 7,766,947 | B2 * | 8/2010 | Hawkes | A61F 2/389 606/280 |
| 7,862,597 | B2 * | 1/2011 | Gause | A61B 17/1728 606/290 |
| 8,083,741 | B2 * | 12/2011 | Morgan | A61B 5/4504 606/280 |
| 8,551,092 | B2 * | 10/2013 | Morgan | A61N 1/205 606/280 |
| 12,661,234 | B2 | 6/2026 | Moses et al. | |
| 2002/0062153 | A1 | 5/2002 | Paul et al. | |
| 2003/0135275 | A1 | 7/2003 | Garcia et al. | |
| 2004/0049270 | A1 | 3/2004 | Gewirtz | |
| 2005/0228503 | A1 | 10/2005 | Gundolf | |
| 2005/0273170 | A1 | 12/2005 | Navarro et al. | |
| 2006/0052782 | A1 * | 3/2006 | Morgan | A61B 5/14539 606/60 |
| 2006/0116678 | A1 * | 6/2006 | Impellizzeri | A61B 17/8057 606/291 |
| 2006/0190080 | A1 * | 8/2006 | Danoff | A61F 2/30721 623/17.11 |
| 2006/0259143 | A1 | 11/2006 | Navarro et al. | |
| 2008/0177330 | A1 * | 7/2008 | Ralph | A61B 17/8047 606/290 |
| 2009/0182432 | A1 | 7/2009 | Zdeblick et al. | |
| 2009/0198284 | A1 * | 8/2009 | Henry | A61B 17/8605 606/329 |
| 2011/0015682 | A1 * | 1/2011 | Lewis | A61B 17/88 606/305 |
| 2011/0118852 | A1 | 5/2011 | Evans | |
| 2011/0224737 | A1 * | 9/2011 | Lewis | A61B 17/8057 606/290 |
| 2013/0052254 | A1 * | 2/2013 | Arinzeh | C12N 5/0618 424/443 |
| 2013/0304211 | A1 | 11/2013 | Trautwein et al. | |
| 2013/0317615 | A1 | 11/2013 | Jimenez et al. | |
| 2014/0025168 | A1 | 1/2014 | Klimek et al. | |
| 2014/0094856 | A1 * | 4/2014 | Sinha | A61B 17/8052 606/291 |
| 2015/0134061 | A1 | 5/2015 | Friis et al. | |
| 2016/0135858 | A1 * | 5/2016 | Dacosta | A61B 17/1728 606/280 |
| 2016/0325241 | A1 * | 11/2016 | May | B01F 23/23121 |
| 2017/0007420 | A1 | 1/2017 | Stevenson et al. | |
| 2018/0110550 | A1 * | 4/2018 | Pengo | A61N 2/002 |
| 2018/0132913 | A1 * | 5/2018 | Davison | A61B 17/8057 |
| 2018/0140339 | A1 * | 5/2018 | Silva | A61B 17/8057 |
| 2018/0303616 | A1 | 10/2018 | Bhattacharyya et al. | |
| 2019/0099276 | A1 | 4/2019 | Chin et al. | |
| 2019/0274838 | A1 | 9/2019 | Manwill et al. | |
| 2020/0129312 | A1 * | 4/2020 | Donahoe | A61B 17/86 |
| 2020/0345399 | A1 * | 11/2020 | Gregory, II | A61B 50/30 |
| 2021/0367134 | A1 | 11/2021 | Friis et al. | |
| 2022/0015811 | A1 * | 1/2022 | Lopez Camacho | A61B 17/7216 |
| 2022/0339429 | A1 * | 10/2022 | Li | A61N 1/04 |
| 2023/0029611 | A1 | 2/2023 | Shanks et al. | |
| 2023/0346437 | A1 * | 11/2023 | Moses | A61B 17/72 |
| 2023/0414365 | A1 | 12/2023 | Davis et al. | |
| 2024/0058504 | A1 | 2/2024 | Johnson et al. | |
| 2025/0018181 | A1 * | 1/2025 | Moses | A61F 2/4455 |
| 2026/0144644 | A1 | 5/2026 | Moses et al. | |

FOREIGN PATENT DOCUMENTS

| | | | | |
|---|---|---|---|---|
| EP | 1023872 | A2 | 8/2000 | |
| WO | WO-2005120203 | A2 * | 12/2005 | A61B 5/4839 |
| WO | WO-2006084239 | A2 * | 8/2006 | A61F 2/30721 |
| WO | 2017062399 | A1 | 4/2017 | |
| WO | 2020231929 | A1 | 11/2020 | |
| WO | 2021052356 | A1 | 3/2021 | |
| WO | WO-2022015696 | A2 * | 1/2022 | A61B 17/7216 |

OTHER PUBLICATIONS

USPTO; Non-Final Office Action issued in U.S. Appl. No. 18/308,406; dated Jun. 16, 2025; 18 pages.
U.S. Patent and Trademark Office, International Search Report and the Written Opinion of the International Searching Authority, or the Declaration, issued in International Patent Application No. PCT/US2023/020208, dated Nov. 6, 2023,18 pages.
EPO; Extended European Search Report issued for EP Patent Application No. 23797281.5 dated Mar. 19, 2026; 14 pages.
EPO; Extended European Search Report issued in EP Patent Application No. 23797284.9, dated Mar. 9, 2026; 7 pages.

* cited by examiner

PIEZOELECTRIC ORTHOPEDIC IMPLANT AND METHODOLOGY

CROSS-REFERENCE TO RELATED APPLICATIONS

This application claims priority from U.S. Provisional Patent Application 63/335,343, filed Apr. 27, 2022, and U.S. Provisional Patent Application 63/396,019, filed Aug. 8, 2022, each of which is hereby incorporated herein by reference in its entirety.

TECHNICAL FIELD

The present invention relates to bone implants, and more particularly to bone implant assemblies and methodologies that include piezoelectric material capable of generating an electrical output that may stimulate bone and tissue growth around the implant.

BACKGROUND ART

A key contributor of success in orthopedic surgery for repair for fractured bones or for spinal fusion is the ability of the patient's body to successfully repair and regrow the bone structure in the region of the fracture, a spinal fusion, or treatment of a bone void defect. It is known that electrical stimulation promotes and stimulates bone growth and bone healing. However, prior art electrical stimulation devices for use after orthopedic surgery often require multiple surgeries for implantation and removal, as they require a battery that requires recharging or replacement. Alternatively, in the case of external stimulation, the patient may be required to wear a stimulation device for large portions of the day.

SUMMARY OF THE EMBODIMENTS

In accordance with one embodiment of the invention, an orthopedic implant assembly includes a bone plate configured to couple the implant assembly to a fractured bone. A piezoelectric layer is incorporated with a bone plate and configured to produce an electrical output corresponding to a load the piezoelectric layer is subjected to. When the piezoelectric layer is in contact with the fractured bone the electrical output is transmitted to the fractured bone.

In accordance with related embodiments of the invention, the fractured bone may be a femur, a tibia, a fibula, a humerus, an ulna, a radius, a vertebra, a bone of the shoulder joint, a bone of the hip joint, and/or a bone of the ankle joint. The load may be an anatomical load. The piezoelectric layer may include polyvinylidene fluoride and/or polyvinylidene difluoride (PVDF). The bone plate may have a bottom surface with undulations and the piezoelectric layer may be disposed on the bottom surface, the bottom surface being configured to compress the piezoelectric layer such that the electrical output of the piezoelectric layer is actuated.

Further in accordance with related embodiments of the invention, the piezoelectric layer may include a lip configured to wrap around an underside of the bone plate. The bone plate may include a slot configured to receive the piezoelectric layer. The bone plate may further include a set of fasteners configured to secure the piezoelectric layer in the slot. In accordance with related embodiments of the invention, the piezoelectric layer may have a shape of a band and may be configured to wrap around the bone plate at a fracture site.

In accordance with another embodiment of the invention, an orthopedic implant assembly includes a first bone plate having a shape suitable for coupling a first side of the implant assembly to a fractured bone and having a second side that is undulated. A piezoelectric layer is disposed between the first bone plate and the second bone plate, and is configured to produce an electrical output corresponding to a load the piezoelectric layer is subjected to. A second bone plate has an underside that is undulated and is disposed on the piezoelectric layer. The piezoelectric layer is compressed between the undulated second side of the first bone plate and the undulated underside of the second bone plate. When at least one of the first bone plate and the second bone plate is in contact with the fractured bone, the electrical output is transmitted to the fractured bone.

In accordance with related embodiments of the invention, the fractured bone may be a femur, a tibia, a fibula, a humerus, an ulna, a radius, a vertebra, a bone of the shoulder joint, a bone of the hip joint, and/or a bone of the ankle joint. The orthopedic implant assembly include a set of fasteners, wherein the first bone plate, the piezoelectric layer, and the second bone plate each have a set of openings, the sets of openings aligned with each other such that each one of the set of fasteners protrudes through the aligned openings into the fractured bone. The set of fasteners may be configured to transmit the electrical output to the fractured bone. A material of each one of the first and second bone plates may be a conductive material and/or a non-conductive material. The load may be an anatomical load. The piezoelectric layer may include polyvinylidene fluoride and/or polyvinylidene difluoride (PVDF).

In accordance with another embodiment of the invention, an orthopedic implant assembly includes a bone plate having a shape suitable for coupling the implant assembly to a fractured bone and having a set of openings and a set of piezoelectric rings, each ring of the set of piezoelectric rings disposed in an opening of the set of openings and configured to produce an electrical output corresponding to a load the ring is subjected to. The assembly further includes a set of fasteners, each fastener to be disposed in one of the set of openings so as to protrude into the fractured bone. The set of fasteners is configured to transmit the electrical output to the fractured bone.

In accordance with related embodiments of the invention, the fractured bone may be femur, a tibia, a fibula, a humerus, an ulna, a radius, a vertebra, a bone of the shoulder joint, a bone of the hip joint, and/or a bone of the ankle joint. A material of the bone plate may be a conductive material, wherein the bone plate is configured to transmit the electrical output to the fractured bone.

In accordance with further related embodiments, the orthopedic implant assembly may include a set of insulator rings, each insulator ring disposed between a corresponding piezoelectric ring and a corresponding opening, wherein a material of each fastener of the set of fasteners is a conductive material, such that the electrical output is transmitted to the fractured bones only by the fasteners. The load may be an anatomical load. The piezoelectric layer may include polyvinylidene fluoride and/or polyvinylidene difluoride (PVDF).

In accordance with another embodiment of the invention, an interspinous process plate for a vertebra is provided. The interspinous process plate includes a first end plate and a second end plate. A center barrel is disposed between and coupled to the first end plate and the second end plate. At least one of the first end plate and the second end plate includes a piezoelectric layer disposed on the end plate and configured to produce an electrical output corresponding to a load the piezoelectric layer is subjected. The center barrel is made from an insulating material. The interspinous process plate is configured to couple to a spinous process of the vertebra and further configured to transmit the electrical output into the spinous process.

In accordance with related embodiments of the invention, at least one the first end plate and the second end plate may include a plurality of teeth configured to engage the spinous process. The piezoelectric layer may include polyvinylidene fluoride and/or polyvinylidene difluoride (PVDF). A surface of the center barrel facing the piezoelectric layer may have undulations, the undulated surface of the center barrel configured to compress the piezoelectric layer such that the electrical output of the piezoelectric layer is actuated.

In accordance with another embodiment of the invention, an interspinous process plate for a vertebra includes a first end plate and a second end plate. An center barrel is disposed between and coupled to the first end plate and the second end plate. The center barrel is made from a piezoelectric material and is configured to produce an electrical output corresponding to a load the implant body is subjected to. The interspinous process plate is configured to couple to a spinous process of the vertebra and further configured to transmit the electrical output into the spinous process.

In accordance with related embodiments of the invention, the at least one of the first end plate and the second end plate includes a plurality of teeth configured to engage the spinous process. The piezoelectric layer may include polyvinylidene fluoride and/or polyvinylidene difluoride (PVDF).

In accordance with another embodiment of the invention, a pedicle screw assembly includes: a body configured to be screwed into a vertebra, a screw head saddle disposed on the body, a piezoelectric layer disposed on the screw head saddle and configured to produce an electrical output corresponding to a load the pedicle screw assembly is subjected to, a rod saddle disposed on the piezoelectric layer, and a head disposed to the rod saddle. The rod saddle has a contoured underside and the screw head saddle has a contoured top surface, the contoured underside and the contoured top surface configured to compress the piezoelectric layer such that the electrical output of the piezoelectric layer is actuated.

In accordance with related embodiments of the invention, the rod saddle may be an insulator. The screw head saddle may be an insulator.

In accordance with another embodiment of the invention, a pedicle screw assembly includes a plurality of pedicle screws, each pedicle screw having a head, a neck, and a body. A rod is coupled to the head of each one of the plurality of pedicle screws. A plurality of piezoelectric layers are each disposed on the neck of a corresponding one of the plurality of pedicle screws and are configured to produce an electrical output corresponding to a load the screws and/or the rod are subjected to. The body of each pedicle screw is configured to be screwed into a vertebra and further configured to transmit the electrical output to the vertebra.

In accordance with related embodiments of the invention, the pedicle screw assembly further includes a piezoelectric rod layer disposed on the rod and configured to produce an additional electrical output corresponding to a load the screws and/or the rod are subjected to. The load may be an anatomical load. The piezoelectric layer may include polyvinylidene fluoride and/or polyvinylidene difluoride (PVDF).

In accordance with another embodiment of the invention, a knee implant assembly includes a tibial implant configured to couple to a tibia and a femoral implant configured to couple to a femur. The tibial implant includes a piezoelectric layer disposed on the implant and configured to produce an electrical output corresponding to a load the implant is subjected to. The knee implant assembly is configured to transmit the electrical output into at least one of the tibia and the femur.

In accordance with related embodiments of the invention, the tibial implant may have an undulated upper surface on which the piezoelectric layer is disposed, configured to compress the piezoelectric layer such that the electrical output of the piezoelectric layer is actuated. The piezoelectric layer may include polyvinylidene fluoride and/or polyvinylidene difluoride (PVDF).

In accordance with another embodiment of the invention, an intramedullary nail assembly includes: a lower shaft having a lower insulated cap; a first piezoelectric ring disposed on the lower insulated cap and configured to produce an electrical output corresponding to a load the intramedullary nail assembly is subjected to; an electrical conductor disposed on the first piezoelectric ring; a second piezoelectric ring disposed on the electrical conductor and configured to produce an electrical output corresponding to a load the intramedullary nail assembly is subjected to; and an upper shaft disposed on the second piezoelectric ring and having an upper insulated cap. The lower insulated cap has a contoured top surface and the upper insulated cap has a contoured underside, the contoured underside and the contoured top surface configured to compress the first and second piezoelectric rings such that the electrical output of the piezoelectric rings is actuated.

In accordance with related embodiments of the invention, the piezoelectric layer includes polyvinylidene fluoride and/or polyvinylidene difluoride (PVDF).

In accordance with another embodiment of the invention, a bone screw assembly includes a body configured to be coupled to a bone, a head, and a washer having a piezoelectric layer disposed therein. The piezoelectric layer is configured to produce and electrical output corresponding to a load the bone screw assembly is subjected to.

In accordance with related embodiments of the invention, the screw head may have undulations configured to actuate the electrical output of the piezoelectric layer. The piezoelectric layer may include polyvinylidene fluoride and/or polyvinylidene difluoride (PVDF).

In accordance with another embodiment of the invention, a hip replacement assembly includes an acetabular component configured to couple to an acetabulum, An articulating surface of the acetabular component has an acetabular piezoelectric layer disposed thereon, the acetabular piezoelectric layer configured to produce a first electrical output corresponding to a load the acetabular piezoelectric layer is subjected to. An insulating liner is disposed on the acetabular piezoelectric layer. A femoral component is configured to couple to a femur and includes a femoral head and a femoral stem. A femoral piezoelectric layer is disposed on the femoral stem and configured to produce a second electrical output corresponding to a load the femoral piezoelectric layer is subjected to. The acetabular component is configured to transmit the first electrical output into the acetabulum, and the femoral component is configured to transmit the second electrical output into the femur.

In accordance with related embodiments of the invention, the acetabular and femoral piezoelectric layers include polyvinylidene fluoride and/or polyvinylidene difluoride (PVDF).

In accordance with another embodiment of the invention, a bone spacer assembly includes: a bottom endplate having a contoured top surface; a first piezoelectric layer disposed on the bottom endplate and configured to produce a first electrical output corresponding to a load the first piezoelectric layer is subjected to; and a top endplate having a contoured bottom surface.

In accordance with related embodiments, a bone spacer assembly may include an insulator disposed on the first piezoelectric layer and having a contoured top surface and a contoured bottom surface; a second piezoelectric layer disposed on the insulator and configured to produce a second electrical output corresponding to a load the second piezoelectric layer is subjected to; The contoured top surface of the bottom endplate and the contoured bottom surface of the insulator are configured to compress the first piezoelectric layer such that the electrical output of the first piezoelectric layer is actuated. The contoured top surface of the insulator and contoured bottom surface of the top endplate are configured to compress the second piezoelectric layer such that the electrical output of the second piezoelectric layer is actuated.

In accordance with related embodiments of the invention, each one of the top endplate, second piezoelectric layer, insulator, and first piezoelectric layer may have a center slot and wherein the bottom endplate may have a raised center portion configured to protrude through the center slots of the first piezoelectric layer, insulator, second piezoelectric layer, and top endplate. The bone spacer assembly may include a set of assembly pins. The top endplate may have a set of pin holes and the raised center portion of the bottom endplate may have a set of expanded holes corresponding to the set of pin holes, such that each one of the set of assembly pins protrudes through one of the set of pin holes and a corresponding one of the set of expanded holes.

In accordance with another embodiment of the invention, a method of making an implant includes the steps of: compressing a first piezoelectric film between a bottom surface of a top endplate and a top surface of an insulator, wherein the bottom surface of the top endplate and the top surface of the insulator have undulations and wherein by applying pressure the first piezoelectric film conforms to the undulations; compressing a second piezoelectric film between a bottom surface of the insulator and a top surface of a bottom endplate, wherein the bottom surface of the insulator and the top surface of the bottom endplate have undulations and wherein by applying pressure the second piezoelectric film conforms to the undulations; drilling a set of pin holes through the top endplate and the bottom endplate; expanding the set of pin holes of the bottom endplate to result in expanded holes, such that a top border of the expanded holes aligns with a top border of the pin holes of the top endplate; and inserting a set of assembly pins through the pin holes of the top endplate and the expanded holes of the bottom endplate such that the first and second piezoelectric films remain compressed.

In accordance with another embodiment of the invention, a method of making an implant includes the steps of: compressing a piezoelectric film between a bottom surface of a top endplate and a top surface of a bottom endplate, wherein the bottom surface of the top endplate and the top surface of the bottom endplate have undulations and wherein by applying pressure the first piezoelectric film conforms to the undulations; drilling a set of pin holes through the top endplate and the bottom endplate; expanding the set of pin holes of the bottom endplate to result in expanded holes, such that a top border of the expanded holes aligns with a top border of the pin holes of the top endplate; and inserting a set of assembly pins through the pin holes of the top endplate and the expanded holes of the bottom endplate such that the piezoelectric film remains compressed.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
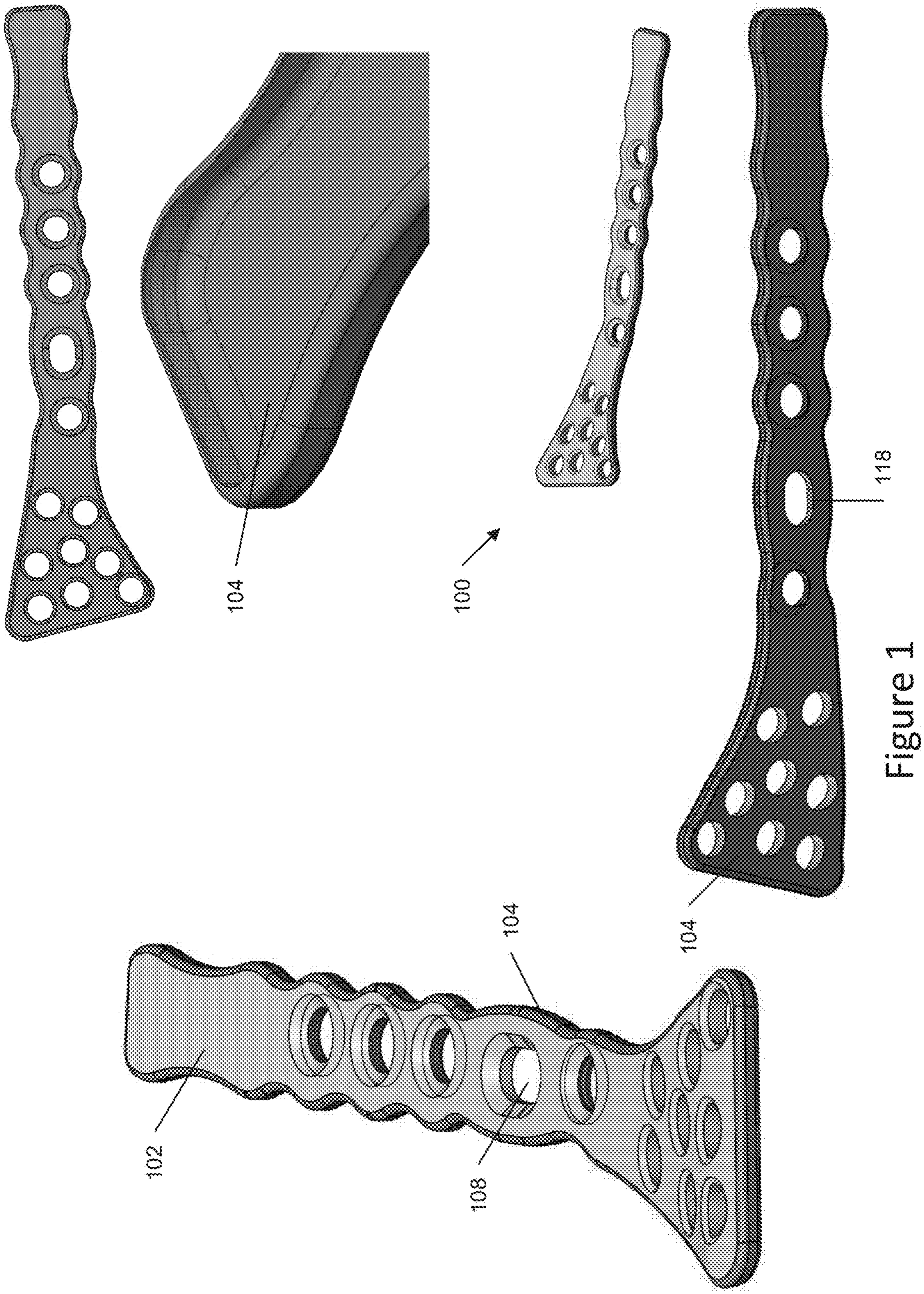
FIG. 1 shows an implant assembly in accordance with an embodiment of the invention.

Definitions. As used in this description and the accompanying claims, the following terms shall have the meanings indicated, unless the context otherwise requires:

A "set" includes at least one member.

In illustrative embodiments of the invention, an implant assembly that includes a piezoelectric material disposed on a bone plate or other suitable frame is provided. The implant assembly may be seated directly on or proximate fractured bone. The stresses placed on the implant assembly, and particularly the piezoelectric material, create an electrical output that is transferred proximate to the fracture so as to promote and stimulate bone growth and bone healing. The piezoelectric material may advantageously be polyvinylidene fluoride or polyvinylidene difluoride (hereinafter PVDF), which is biocompatible and can be used in prolonged, direct contact with body tissue. Other piezoelectric materials, as known in the art, may also be used. Details are provided below.

Piezoelectric materials are known to have varying levels of response depending on the direction and magnitude of the force applied. The force may be about 10 N, 25 N, 50 N, 100 N, 200 N, 500 N, 700 N, 1000 N, 1500 N, 3000 N, 5000 N, or 10,000 N. The force may be variable and range between an upper and lower bound. The electrical output may include a voltage of about 0.1 mV, 0.3 mV, 0.5 mV, 1 mV, 10 mV, 25 mV, 100 mV, 200 mV, 500 mV, 700 mV, 1 V, 2 V, 3 V, 4 V, 5 V, 6 V, 7 V, 10 V, 15 V, or 20 V. The electrical voltage output may be variable and range between an upper and lower bound. The electrical output may include a current of about 50 nA, 100 nA, 500 nA, 1000 nA, 3000 nA, 5000 nA, 7000 nA, 10,000 nA, 50,000 nA, 100,000 nA, 250,000 nA, 500,000 nA, 750,000 nA, 1 mA, 5 mA, 10 mA, 15 mA, 25 mA, 35 mA, or 50 mA. The electrical current output may be variable and range between an upper and lower bound. All ranges between any of the above values are hereby disclosed. Stress is commonly broken into directional components and described by a 3 by 3 "Cauchy stress tensor" matrix, where d11, d22, and d33 are axial compression along the x, y, and z axes respectively.

The embodiments described in this application are directed to several novel designs for an implant that resolves common biomechanical loading scenarios into planar shear stress on the piezoelectric material, to actuate the resulting electrical signal. For example, by conforming the piezoelectric material to a novel wave or other nonplanar shape, not only does this wave shape increase the total area of piezoelectric material that can be loaded, but it also orients much of that material at a 30 to 60 degree angle relative to the vertical axis. This means that when a patient walks or bends forward and subjects the implant to a simple compressive or shear load, most of the piezoelectric material will actually experience planar shear stress. This design creates a significant advantage in the performance of the end product. This application may describe components with contoured surfaces. Unless described otherwise, contoured surfaces may include non-planar surfaces such as undulations, waves, zig-zags, curves, creases, bends, any combination of these, or any structural geometry which results in uneven application of force.

FIG. 1 shows an implant assembly in accordance with an embodiment of the invention. Implant assembly 100 includes a bone plate or trauma plate 102. The bone plate 102 may be manufactured from titanium or from any other material suitable for use in an orthopedic implant. The bone plate 102 is configured to couple to a fractured bone (not shown) and has a shape suitable for coupling to the fractured bone. A piezoelectric cover layer 104 is configured to be disposed on the bone plate 102. The piezoelectric layer 104 produces an electrical output corresponding to a load, for example an anatomical load, that the piezoelectric layer is subjected to. As described above, the piezoelectric layer 104 illustratively may be manufactured from polyvinylidene fluoride or polyvinylidene difluoride (hereinafter PVDF), or from any other piezoelectric material suitable for use in an orthopedic implant. By way of example, the shape of the piezoelectric layer 104 corresponds to the shape of the bone plate 102 so that the piezoelectric layer 104 wraps around the underside of the bone plate 102. For example, the piezoelectric layer 104 may have a lip along its edge so that the piezoelectric layer 104 encapsulates the bottom and sides of the bone plate 102. The implant assembly 100 may further include a set of openings 108 and 118 for coupling the implant assembly to a fractured bone. Openings 108 may be found in the bone plate 102 and/or openings 118 may be found in the piezoelectric layer 104. When coupling the implant assembly to the fractured bone, openings 108 and 118 may be aligned such that each member of the set of openings 108 corresponds to a member of the set of openings 118.

The implant assembly 100 is configured to be coupled to a fractured bone using a set of fasteners, as shown below with reference to FIG. 6. Each fastener of the set of fasteners corresponds to one of the aligned openings 108 and 118. The fasteners, by way of example, may be lag screws, and the openings 108 and 118 may be threaded. However, it is expressly contemplated that any other fastener suitable for use in an orthopedic implant may be used.

Figure 2:
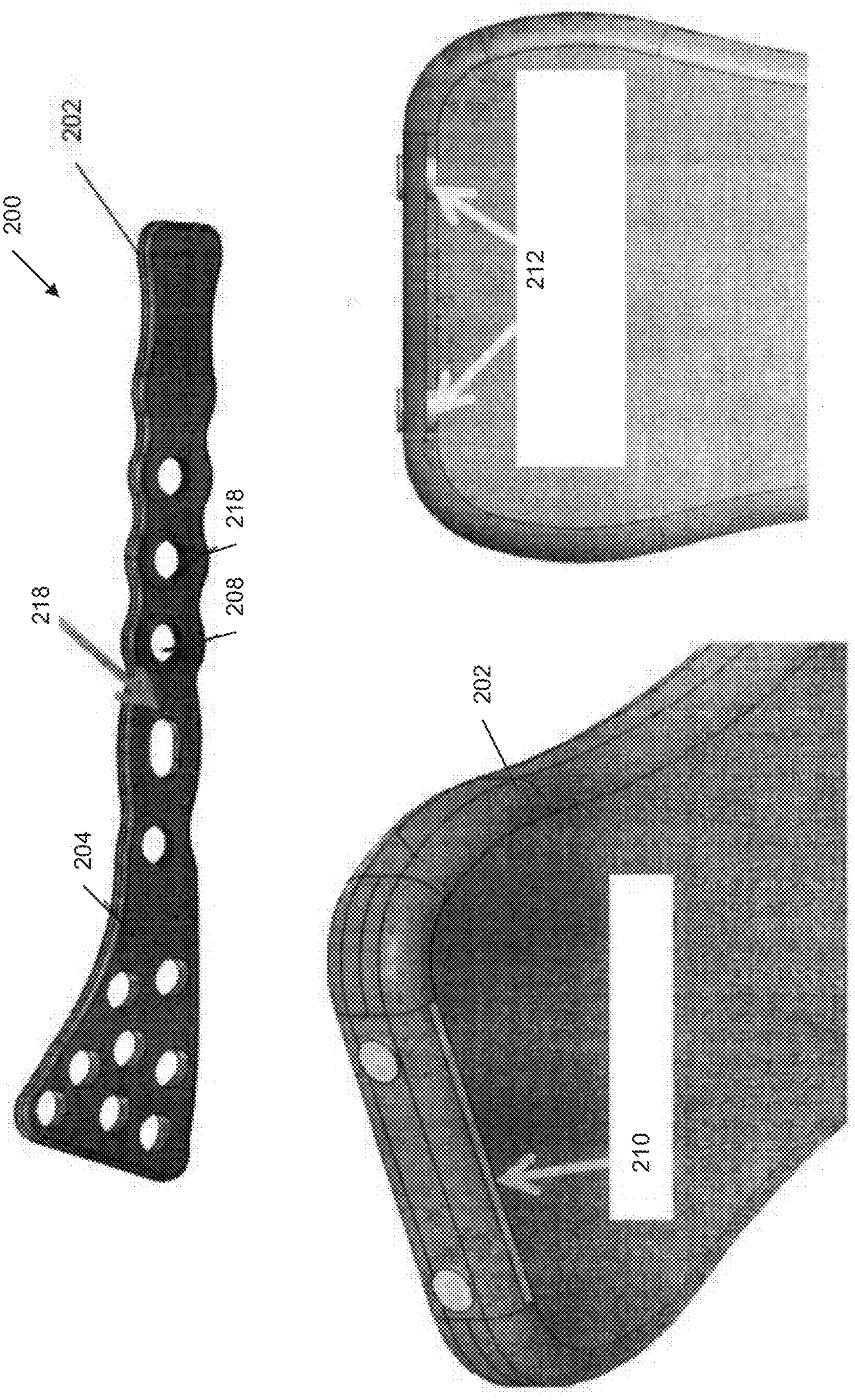
FIG. 2 shows an implant assembly in accordance with an embodiment of the invention.

FIG. 2 shows an implant assembly in accordance with an embodiment of the invention. Implant assembly 200 includes a bone plate 202 and a piezoelectric layer 204. The bone plate 202 includes a slot 210 into which the piezoelectric layer 204 is inserted. The bone plate 202 may also include fasteners 212 that are configured to secure the piezoelectric layer 204 in the slot 210. These fasteners 212 may be, for example, pins or screws. The piezoelectric layer 204 is configured to produce an electrical output corresponding to a load, for example an anatomical load, that the piezoelectric layer is subjected to. The shape of the piezoelectric layer 204 corresponds to the shape of the bone plate 202 so that the piezoelectric layer 204 can be inserted into the slot 210. The implant assembly 200 further includes a set of openings 208 and/or 218 for coupling the implant assembly to a fractured bone. Openings 208 may be found in the bone plate 202, and/or openings 218 may be found in the piezoelectric layer 204. When coupling the implant assembly to the fractured bone, openings 208 and 218 may be aligned such that each member of the set of openings 208 corresponds to a member of the set of openings 218.

Figure 3:
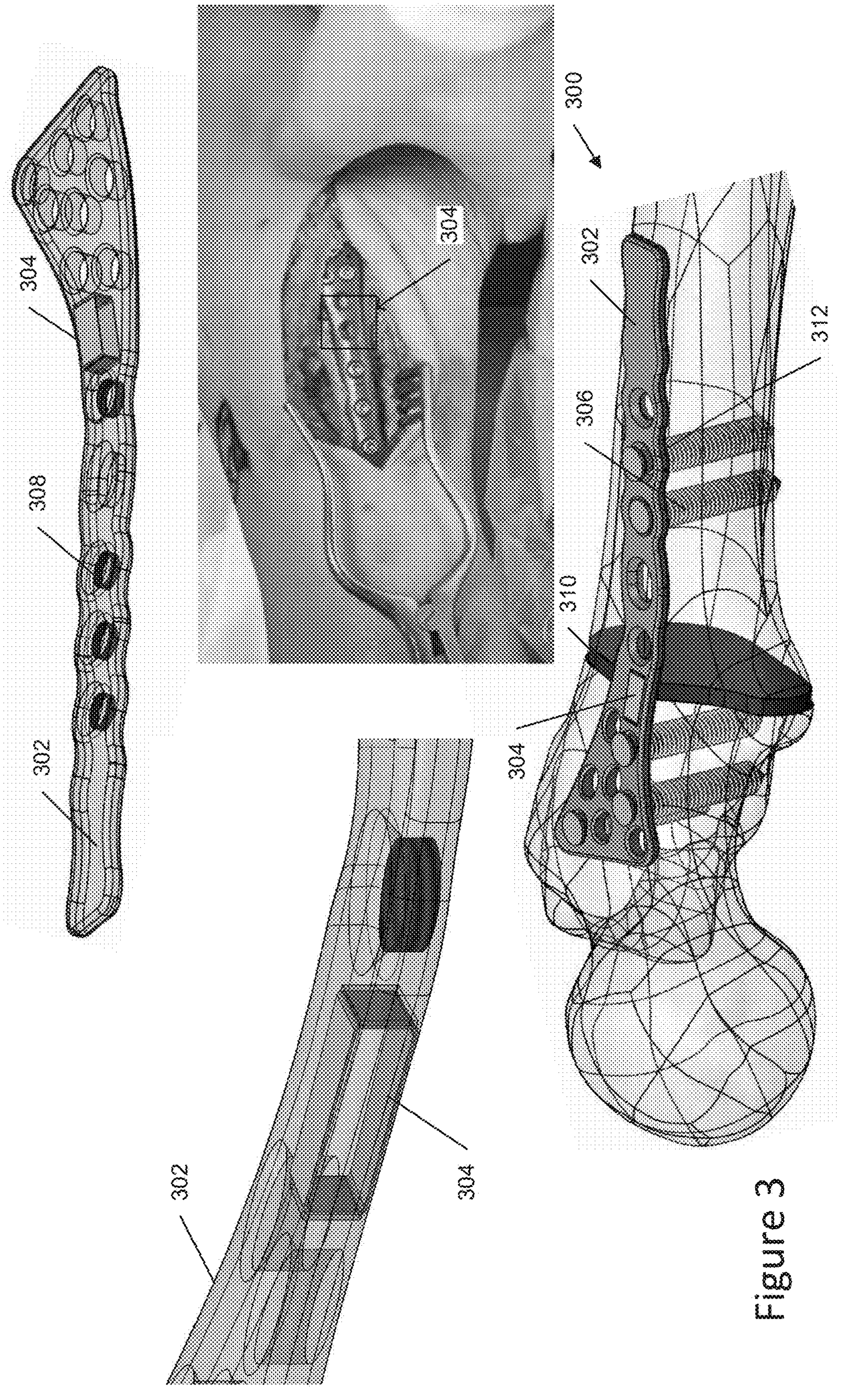
FIG. 3 shows an implant assembly in accordance with an embodiment of the invention.

FIG. 3 shows an implant assembly in accordance with an embodiment of the invention. Implant assembly 300 includes a bone plate 302 and a piezoelectric band 304. The piezoelectric band 304 is preassembled on the bone plate 302 and is located at a common fracture site. The piezoelectric band 304 is configured to produce an electrical output corresponding to a load, for example an anatomical load, that the piezoelectric layer is subjected to. The implant assembly 300 further includes a set of openings 308 for coupling the implant assembly to a fractured bone 312 using a set of fasteners 306. When coupling the implant assembly 300 to the fractured bone 312, the piezoelectric band 304 may be positioned so that it spans a fracture site 310.

Figure 4:
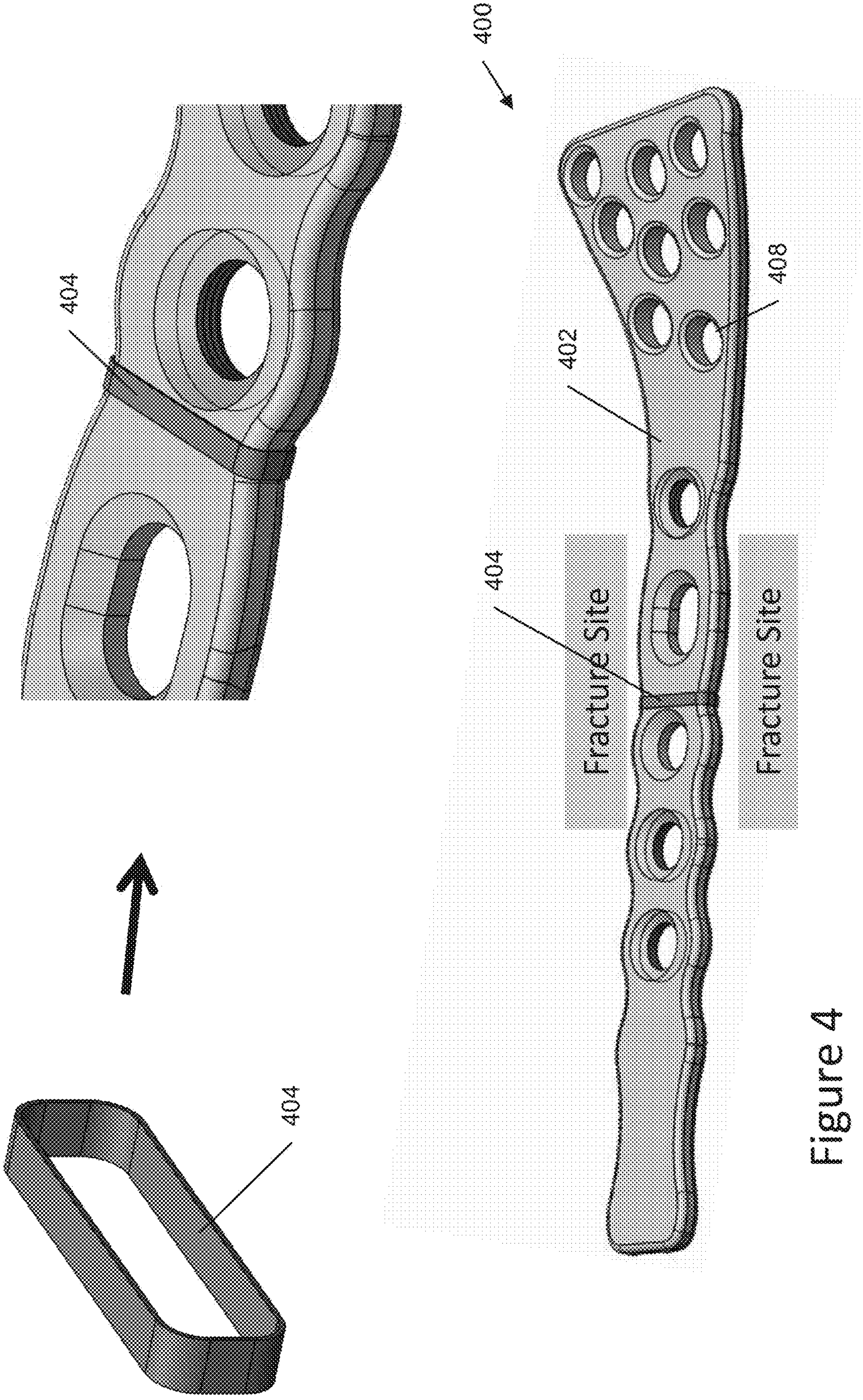
FIG. 4 shows an implant assembly in accordance with an embodiment of the invention.

FIG. 4 shows an implant assembly in accordance with an embodiment of the invention. Implant assembly 400 includes a bone plate 402 and a piezoelectric band 404. The bone plate 402 includes a set of openings 408 for coupling the implant assembly to a fractured bone. The piezoelectric band 404 is configured to slide over or fasten to the bone plate 402 so that it can sit between two openings 408 in the area of a fracture. The piezoelectric band 404 is configured to produce an electrical output corresponding to a load, for example an anatomical load, that the piezoelectric layer is subjected to. When coupling the implant assembly 400 to a fractured bone (not shown), the piezoelectric band 404 may be positioned so that it is located on or spans the fracture site.

Figure 5:
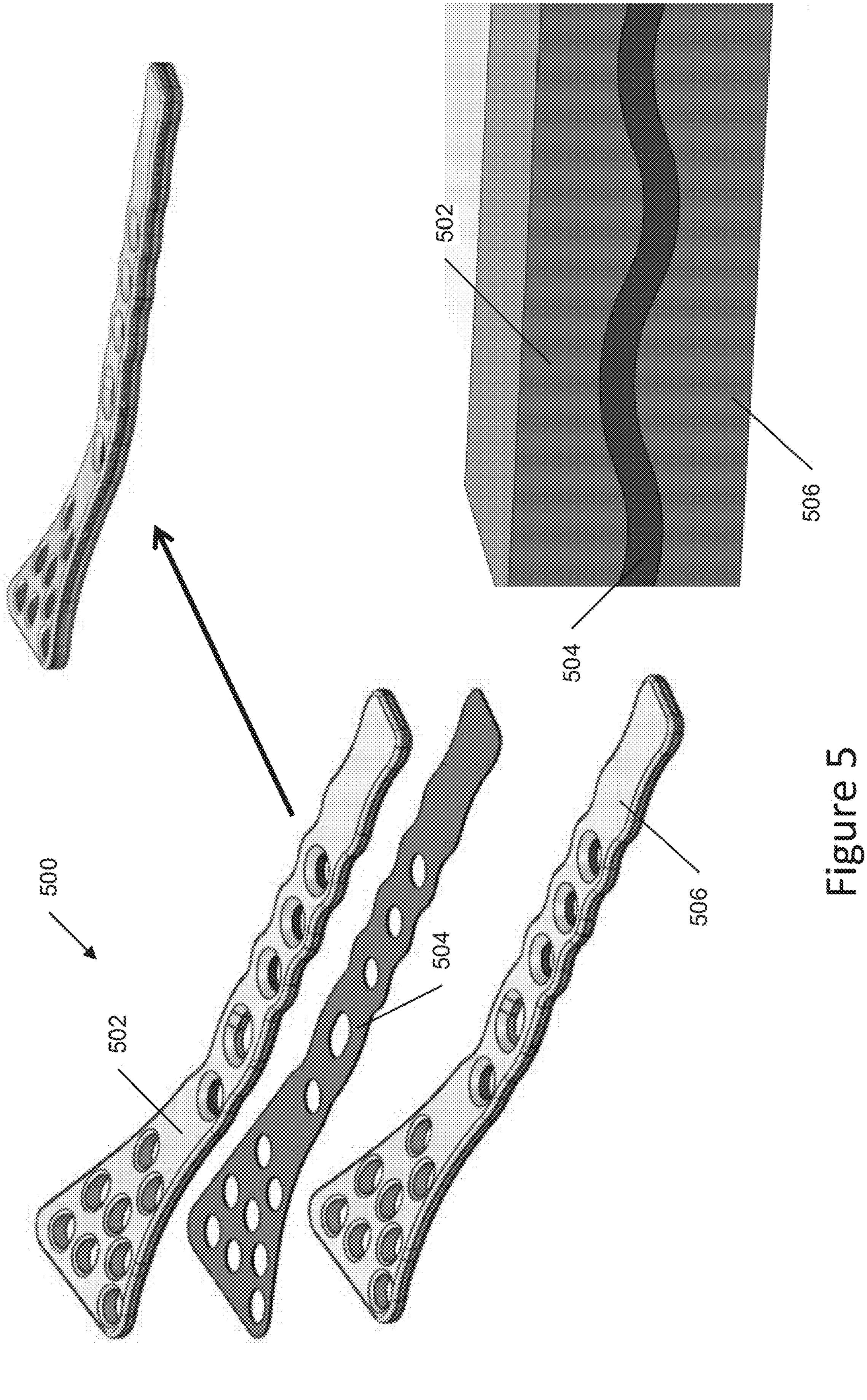
FIG. 5 depicts an implant assembly in accordance with an embodiment of the invention.

FIG. 5 depicts an implant assembly in accordance with an embodiment of the present invention. Implant assembly 500 includes a first bone plate 502, optionally a second bone plate 506, and a piezoelectric layer 504 either coupled to the first bone plate 502 or sandwiched between the first and second bone plates 502 and 506. At least one of the first and second bone plates is configured to couple the implant assembly 500 to a fractured bone (not shown). The first bone plate 502 is disposed on the piezoelectric layer 504, and the piezoelectric layer 504 is disposed on the second bone plate 506. By way of example, bone plates 502 and 506 and piezoelectric layer 504 have the same shape, suitable for coupling to the fractured bone. The first bone plate 502 has a lower surface that is coupled to an upper surface of the piezoelectric layer 504. These surfaces may be flat, or they may be undulated in a direction of the long axis of the first bone plate and/or the short axis of the first bone plate. The surfaces may be in another non-planar shape and configured such that forces applied to the bone plates 502 and 506 cause the piezoelectric layer 504 to have a non-planar shape. Such non-planar shapes include undulations, waves, zig-zags, curves, bends, corners, or creases, oriented in any direction. It is also disclosed that other embodiments within this disclosure may also have these features. The surfaces may be smooth, or they may contain any number of sharp features. The piezoelectric layer 504 also have a lower surface that is coupled to an upper surface of the second bone plate 506. These surfaces may be flat, or they may be undulated in a direction of the long axis of the second bone plate and/or the short axis of the second bone plate. The surfaces may be smooth, or they may contain any number of sharp features. First bone plate 502 and second bone plate 506 may be made from conductive materials, insulating materials, and combinations thereof. The piezoelectric layer 504 is configured to produce an electrical output corresponding to a load, for example an anatomical load, that the piezoelectric layer is subjected to.

Figure 6:
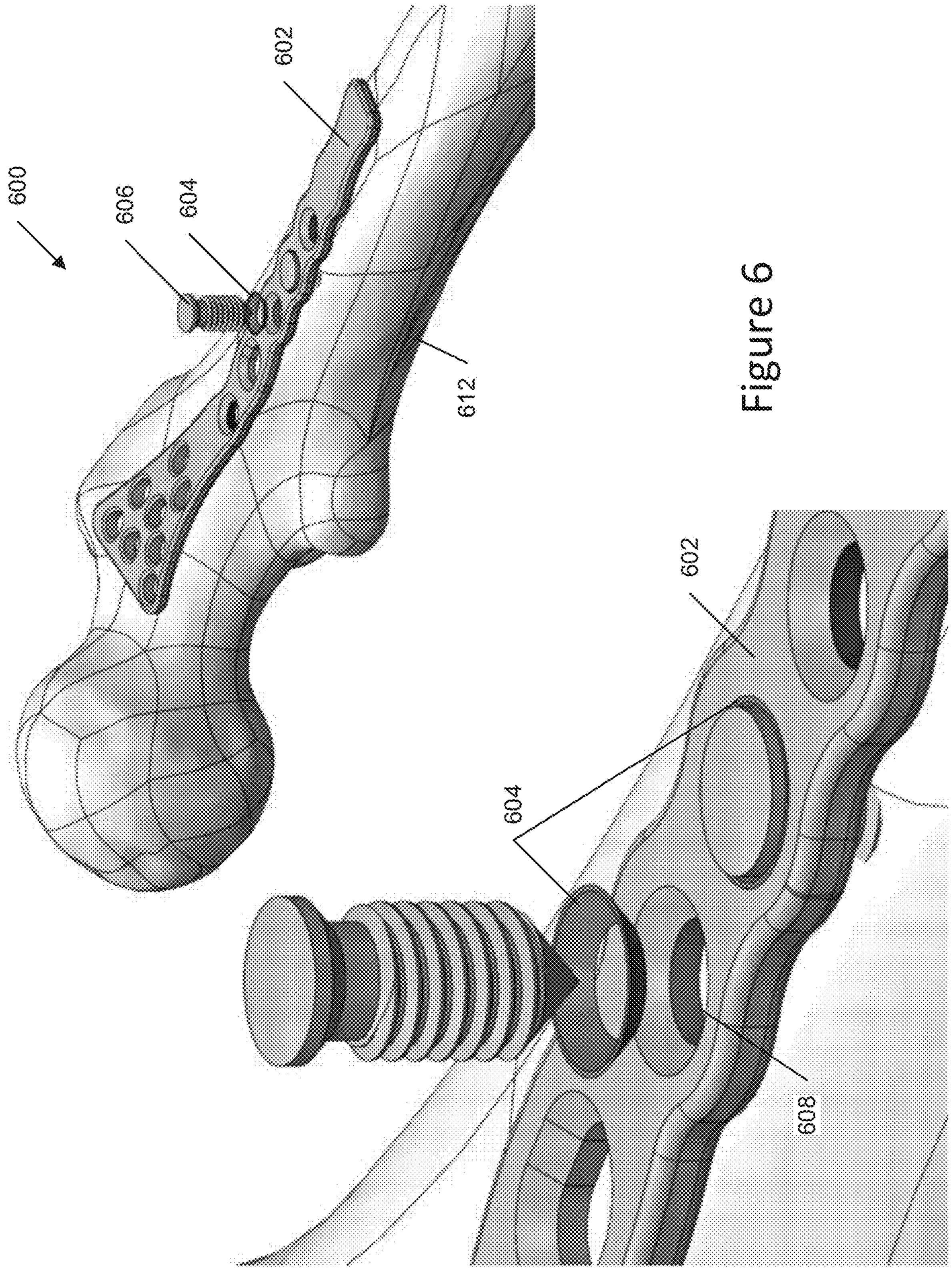
FIG. 6 shows an implant assembly in accordance with an embodiment of the invention.

FIG. 6 shows an implant assembly in accordance with an embodiment of the present invention. Implant assembly 600 includes a bone plate 602 that is configured to couple to a fractured bone 612. The bone plate 602 has set of threaded or unthreaded openings 608 that are configured to be used together with fasteners such as lag screws 606 to affix the implant assembly 600 to the bone 612. At least one of the openings 608 has a piezoelectric ring 604 that is disposed in the opening 608. The piezoelectric ring 604 is configured to produce an electrical output corresponding to a load, for example an anatomical load, that the piezoelectric ring is subjected to. The piezoelectric ring 604 illustratively may be manufactured from PVDF.

Figure 7:
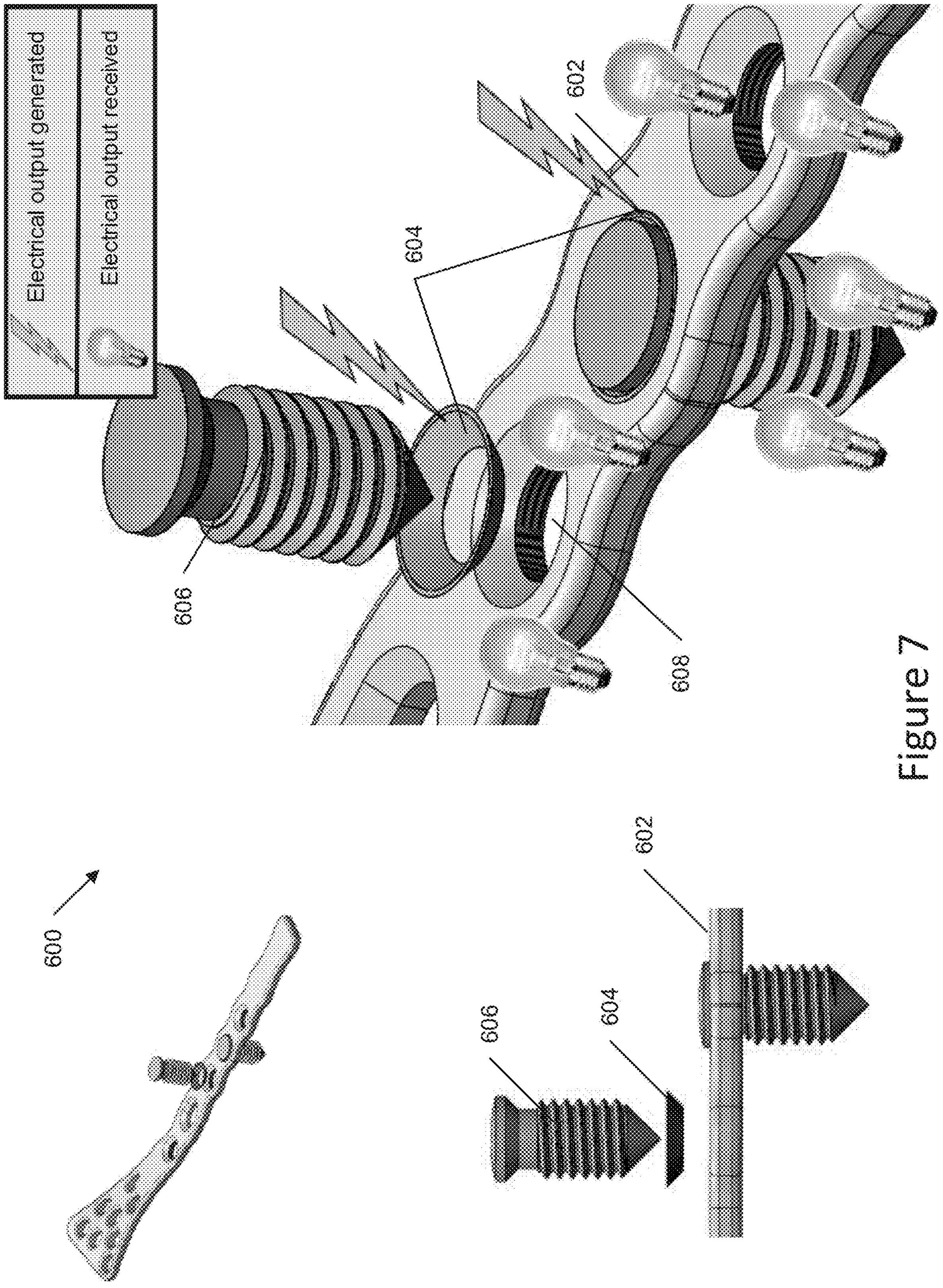
FIG. 7 depicts an implant assembly in accordance with an embodiment of the invention.

FIG. 7 depicts an implant assembly in accordance with an embodiment of the present invention. Bone plate 602 of implant assembly 600 is affixed to bone 612 by lag screws 606 or other types of fasteners. At least one piezoelectric ring 604 is disposed in a corresponding one of the openings 608 so that the lag screw 606 is screwed into the bone 612 through opening 608 and is in electrical contact with the piezoelectric ring 604. Bone plate 602 and/or lag screws 606 are made from a conductive material. In this example, the bone plate 602 and the lag screws 606 transmit the energy generated by the piezoelectric rings 604 into the bone 612. By varying the length of the lag screws, the region of the bone 612 into which the screws 606 transmit the electricity can be selected.

Figure 8:
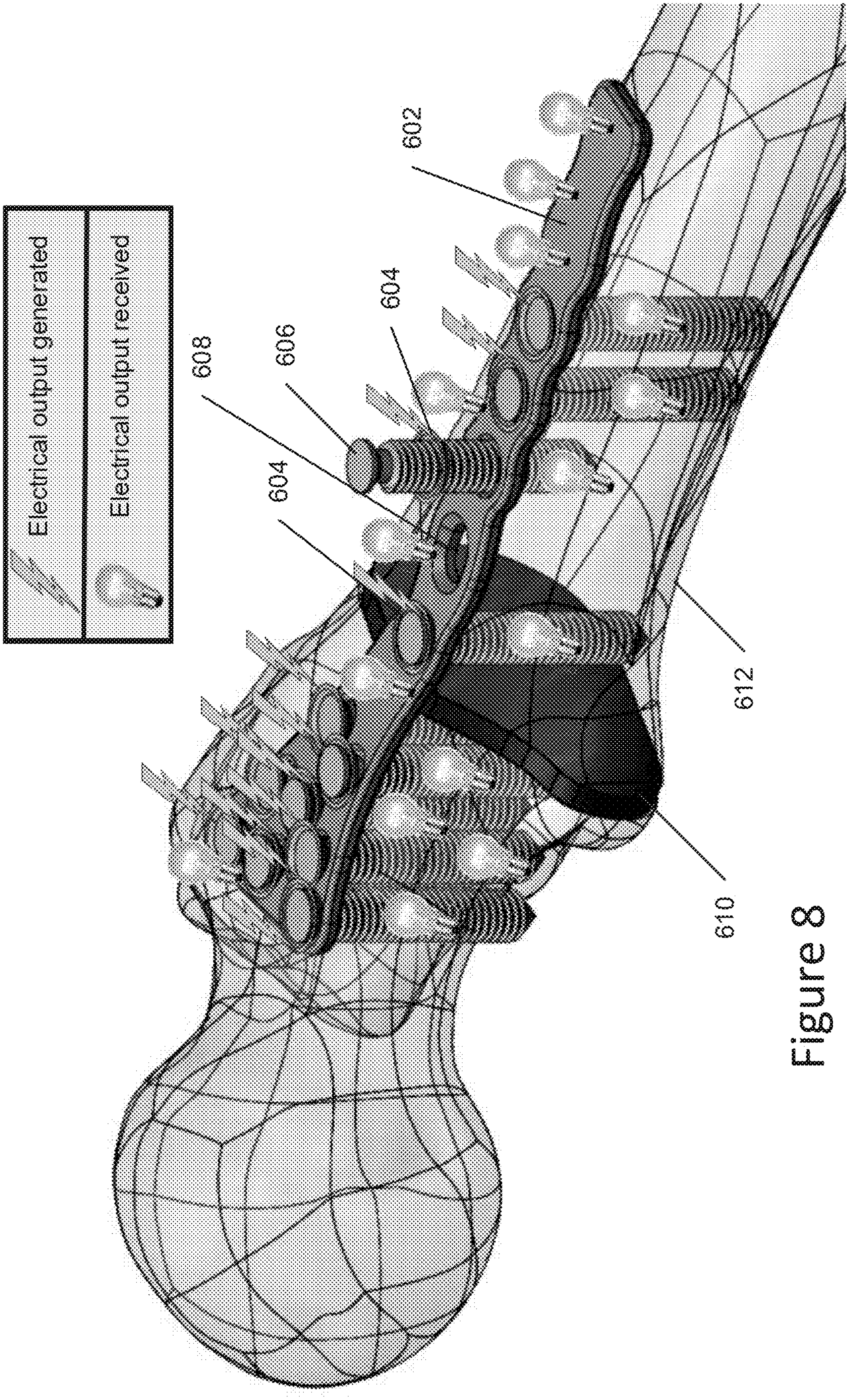
FIG. 8 shows an implant assembly in accordance with an embodiment of the invention.

FIG. 8 shows another view of implant assembly 600 in accordance with an embodiment of the present invention. As described above, the bone plate 602 and the lag screws 606 transmit the energy generated by the piezoelectric rings 604 into the bone 612 in the area of the fracture 610 to stimulate bone growth.

Figure 9:
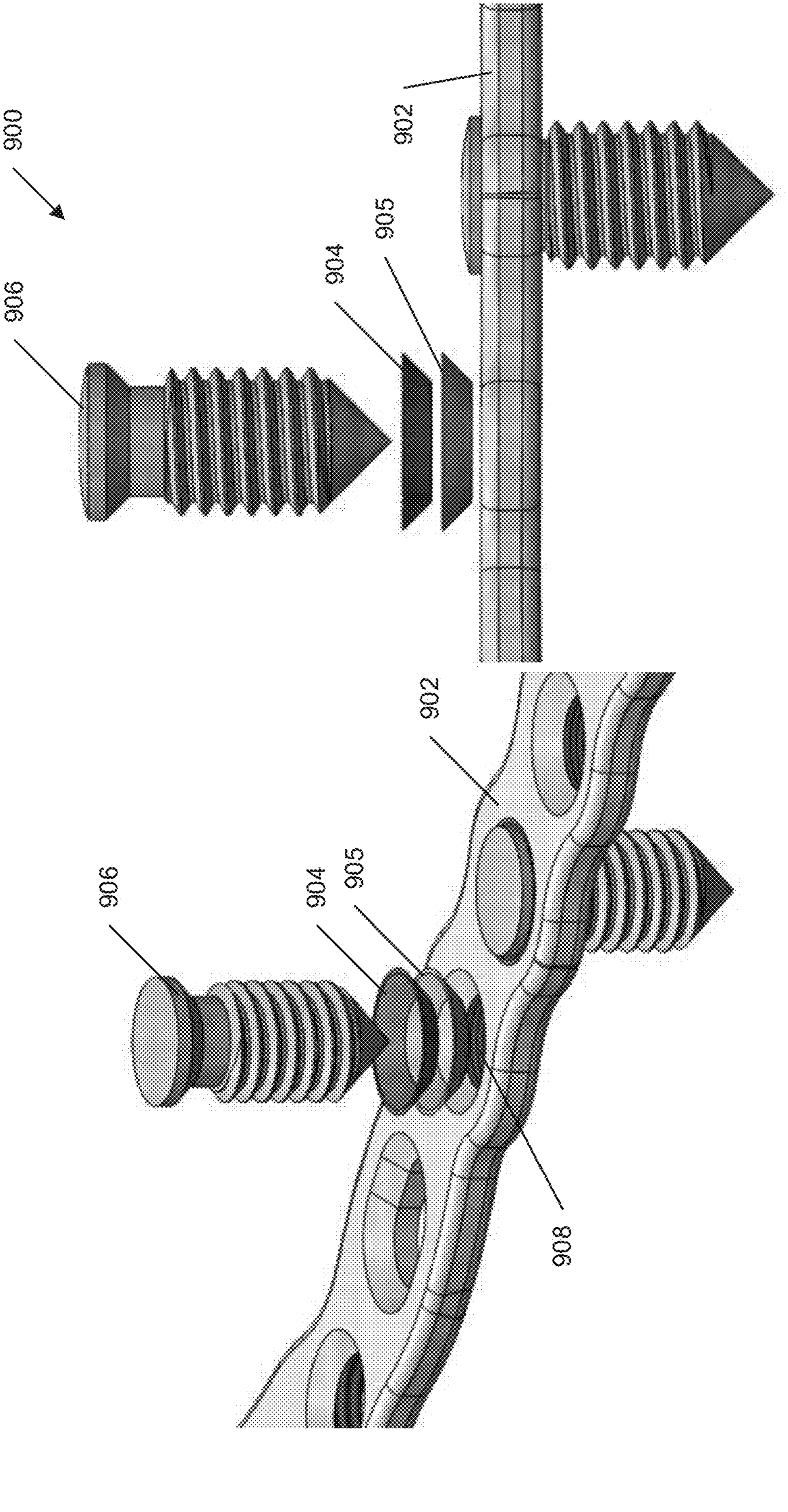
FIG. 9 depicts an implant assembly in accordance with an embodiment of the invention.

FIG. 9 shows an implant assembly in accordance with an embodiment of the present invention. Implant assembly 900 includes bone plate 902 that is configured to couple to a fractured bone. The bone plate 902 has set of threaded or unthreaded openings 908 that are configured to be used together with lag screws 906, or other types of fasteners, to affix the implant assembly 900 to the bone. At least one of the openings 908 has a piezoelectric ring 904 that is disposed in the opening 908. The piezoelectric ring 904 is configured to produce an electrical output corresponding to a load, for example an anatomical load, that the piezoelectric ring is subjected to. The piezoelectric ring 904 illustratively may be manufactured from PVDF. The piezoelectric ring 904 is disposed on an insulator ring 905, which is made from an insulating material. The insulator ring 905 prevents electricity produced by the piezoelectric ring 904 to be transmitted to the bone plate 902.

Figure 10:
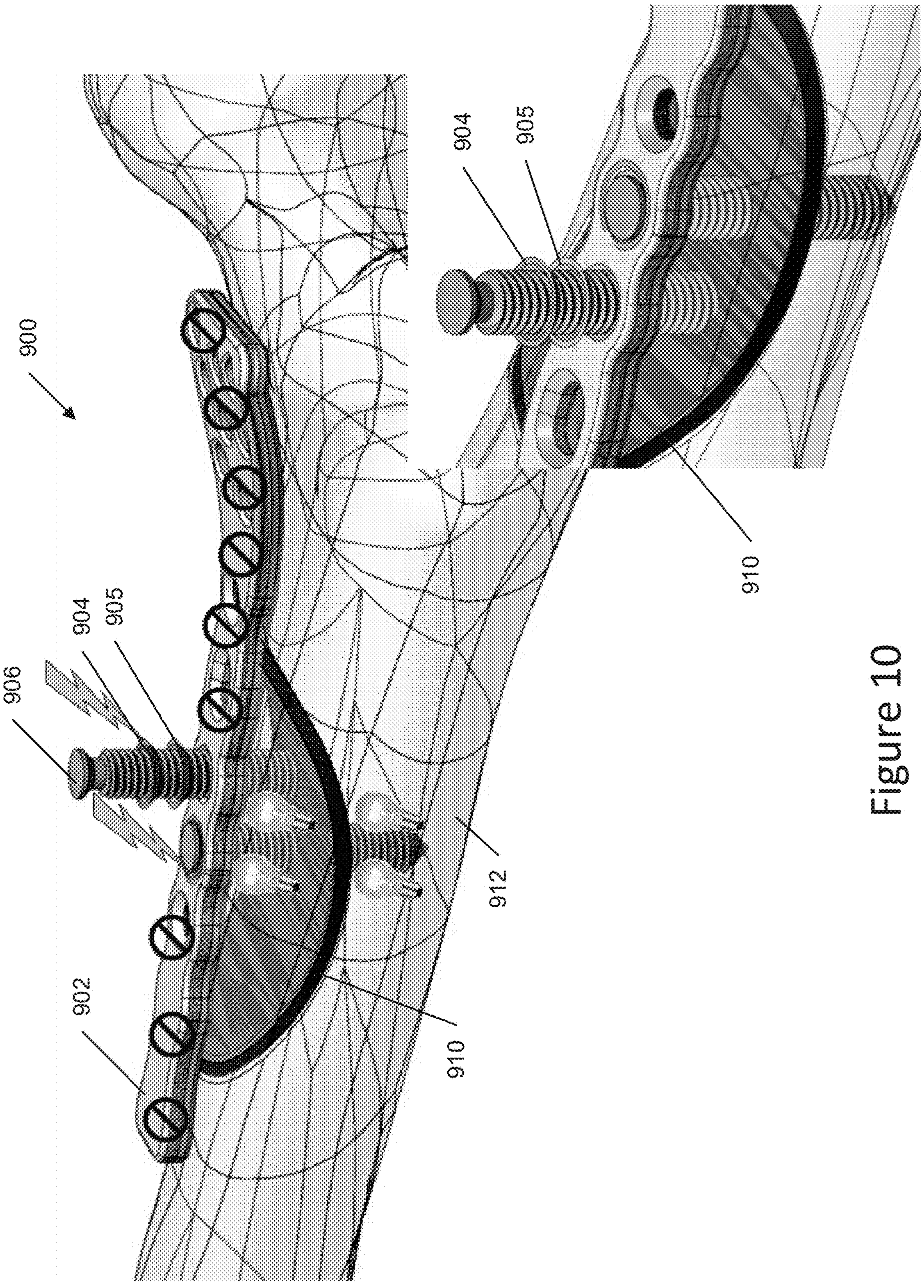
FIG. 10 shows an implant assembly in accordance with an embodiment of the invention.

FIG. 10 depicts another view of implant assembly 900 in accordance with an embodiment of the present invention. The implant assembly 900 is affixed to fractured bone 912 in a region across the fracture 910. Electric energy generated by the piezoelectric ring 904 is transmitted to the bone 912 through lag screw 906 (or another type of fastener), which is made from a conductive material. The insulator ring 905 prevents electric energy to be transmitted to the bone plate 902, so that the electrical charge is focused across the fracture through the set of lag screws 906.

Figure 11:
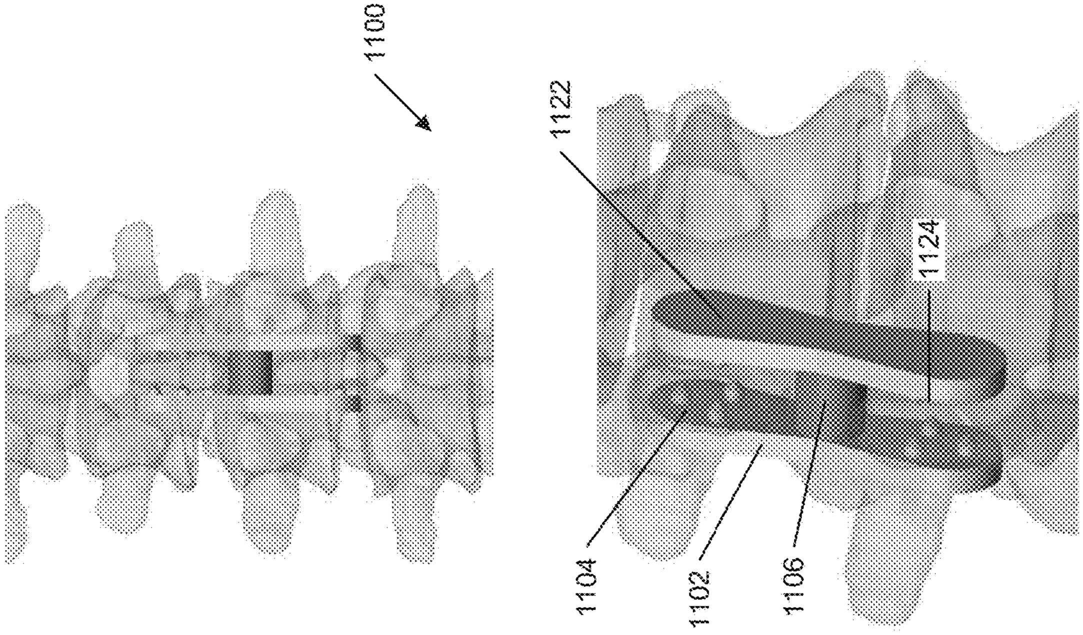
FIG. 11 shows an interspinous process fixation plate in accordance with an embodiment of the invention.

FIG. 11 shows an interspinous process fixation plate in accordance with an embodiment of the present invention. Interspinous process fixation plate 1100 includes a first end plate 1102, a second end plate 1122, which is coupled to the first end plate by a center barrel 1106, and at least one layer of piezoelectric material. In this embodiment, the implant 1100 includes a first and second layer of piezoelectric material 1104 and 1124. The first layer of piezoelectric material 1104 is disposed on the first end plate 1102 and faces the center barrel 1106. The second layer of piezoelectric material 1124 is disposed on the second end plate 1122 and faces the center barrel 1106. Exemplarily, the components of the implant 1100 may be joined together using a set of tantalum screws (not shown), which are excellent conductors. However, it should be understood that the components may be adjoined using any other suitable material, structure, or method, such as a tantalum rod, saturation or dispersion, coating, rivets, adhesive, friction fit, swing lock, or a combination thereof.

The first end plate 1102 and the second end plate 1122 are typically made of titanium, or other suitable material. The end plates may include a plurality of teeth ranging from 0.5 mm to 5 mm in height, and protruding vertically from an outer surface of the plates. The teeth are configured to engage the spinous process, thereby affixing or securing the implant 1100 to the spinous process. The center barrel 1106 may be made of a suitable polymer material, such as polyether ether ketone (PEEK), which is an excellent insulator, capable of insulating the electrical current produced by the piezoelectric material and providing visibility for post operation evaluation. However, it is also expressly contemplated that the center barrel 1106 may be made of a piezoelectric material, such as PVDF. The first and second layers of piezoelectric material 1104 and 1124 are made from PVDF film, or other piezoelectric material, and are disposed between each end plate 1102, 1122 and the center barrel 1106. The layers 1104 and 1124 generally mold to the shape of the surfaces between which they are disposed. The first and second piezoelectric layers 1104 and 1124 are configured to produce an electrical output corresponding to a load, for example an anatomical load, that the respective piezoelectric layer is subjected to. One or both of the surfaces of the center barrel 1106 that face the piezoelectric layers may be contoured to increase the electrical output generated by the piezoelectric layers and/or the center barrel.

Figure 12:
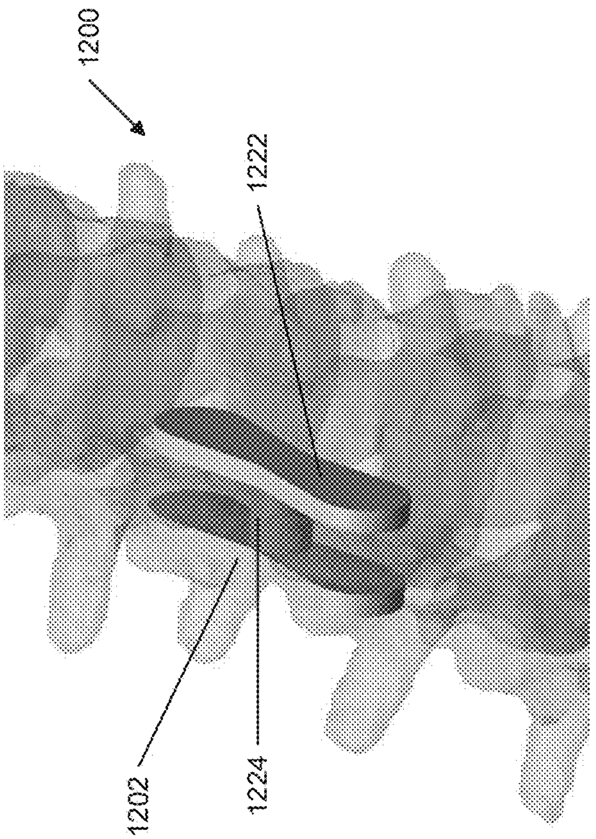
FIG. 12 depicts a dynamic interspinous process fixation plate in accordance with an embodiment of the invention.

FIG. 12 shows a dynamic interspinous process plate in accordance with an embodiment of the present invention. Interspinous process fixation plate 1200 includes a first end plate 1202 and a second end plate 1222. The first end plate 1202 is coupled to the second end plate 1222 by a center barrel 1224. The first and second end plates 1202 and 1222 may be made of titanium or other suitable material. At least one of the first and second end plates 1202 and 1222 may have no teeth to preserve motion of the interspinous process fixation plate 1200 relative to the spinous processes and/or vertebrae of the spinal column. Alternatively, the first and second end plates may have teeth as described above with reference to FIG. 11. The center barrel 1224 is made from PVDF, or other piezoelectric material, and is configured to produce an electrical output corresponding to a load, for example an anatomical load, that the implant body is subjected to.

Figure 13A:
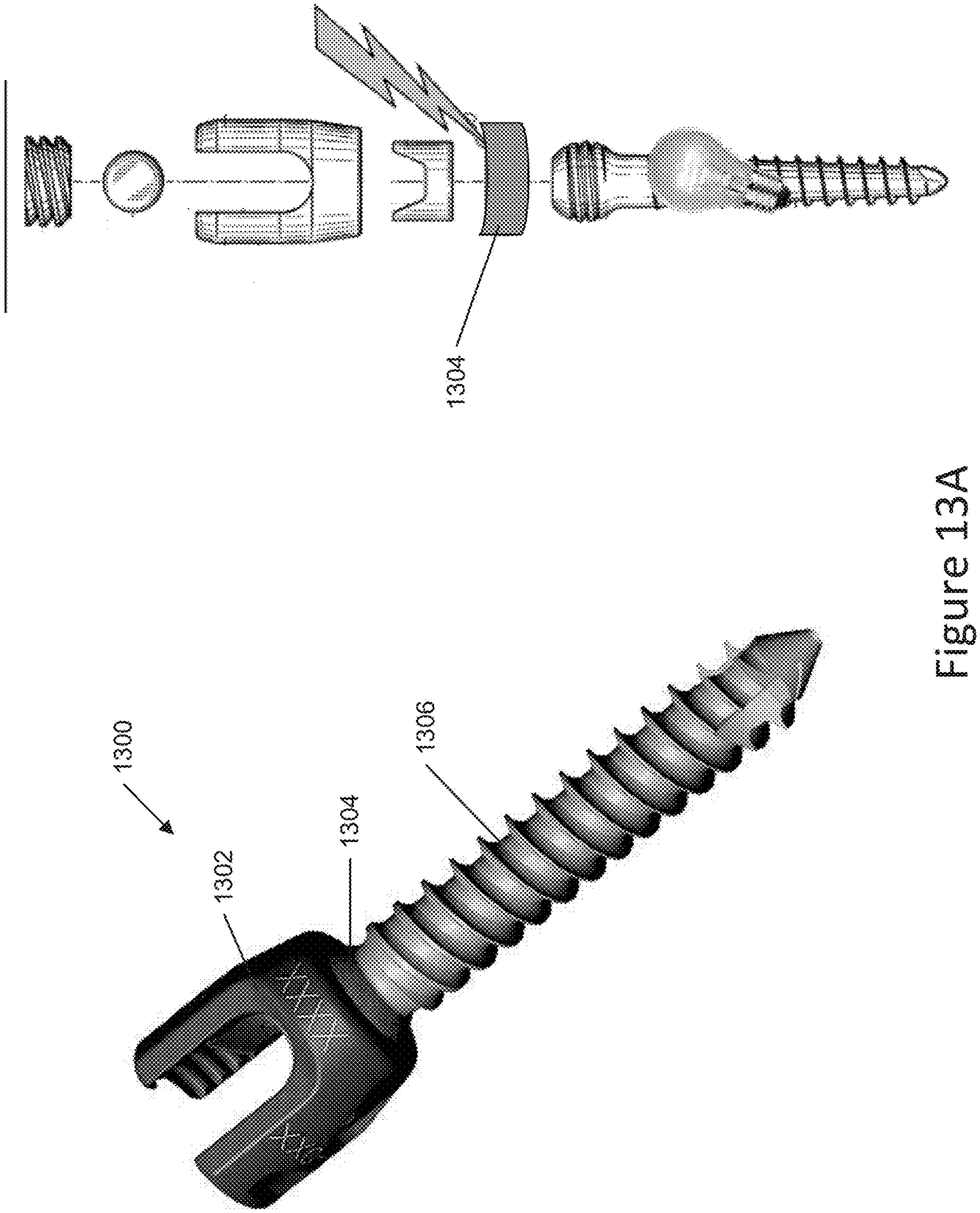
FIG. 13A shows a pedicle screw assembly in accordance with an embodiment of the invention.
Figure 13B:
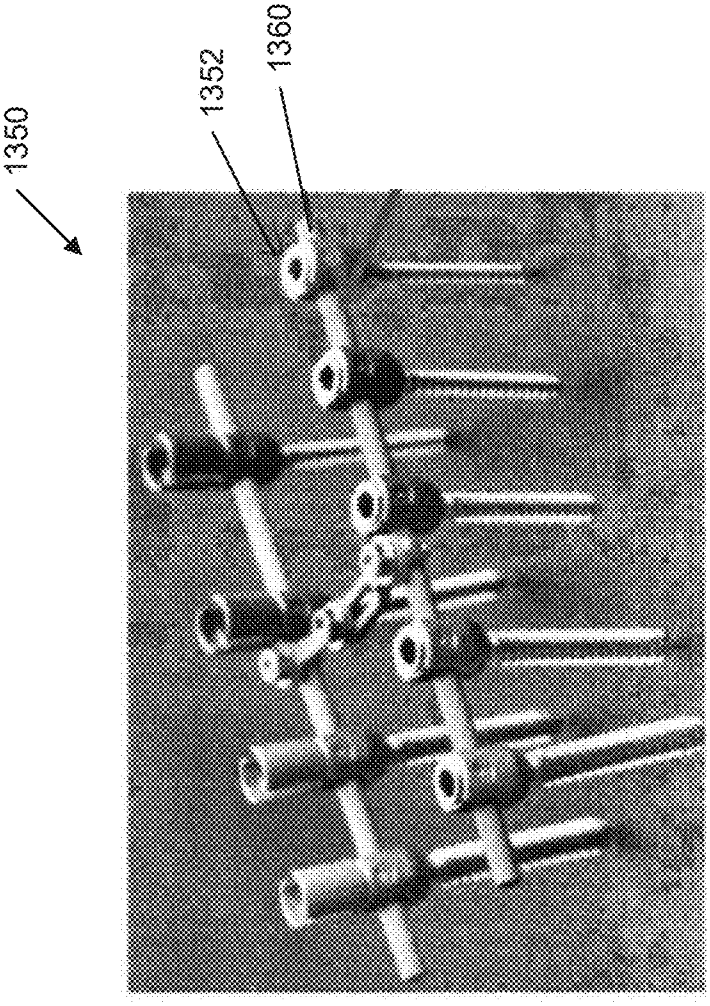
FIG. 13B shows a pedicle screw assembly in accordance with an embodiment of the invention.

FIG. 13A shows a pedicle screw assembly in accordance with an embodiment of the present invention. Pedicle screw 1300 is configured to be screwed into a vertebra. The pedicle screw 1300 has a head 1302, a neck, and a body 1306. The head 1302 is coupled to the body 1306 by the neck. To this end, the neck may, for example, be attached to the body and may be threaded so that the head can be screwed onto the neck and thereby coupled to the body. The body 1306 is configured to be screwed into the vertebra. The head 1302 also includes an opening by which the screw 1300 can be attached to a rod, as shown in FIG. 13B. A piezoelectric layer 1304 is disposed on the neck. The piezoelectric layer 1304 may be made from PVDF, or other piezoelectric material, and is configured to produce an electrical output corresponding to a load, for example an anatomical load, that the pedicle screw is subjected to. The neck and/or body of the pedicle screw 1300 are made from a conductive material so that the electrical output from the piezoelectric layer 1304 is transmitted through neck and body of the pedicle screw 1300 into the vertebra. The head 1302 may also made from a conductive material and is electrically coupled to the neck and body.

FIG. 13B shows a pedicle screw assembly 1350 in accordance with an embodiment of the present invention. A plurality of pedicle screws 1352, which are configured similar to the pedicle screws 1300 described above, are connected by a rod 1360. The rod 1360 is coated with a layer of PVDF or other piezoelectric material, and is configured to enhance posterior lateral fusion of the vertebrae the assembly 1350 is coupled to. As described above in reference to FIG. 13A, each pedicle screw 1352 also includes a neck onto which a PVDF layer or other piezoelectric material, is disposed. The rod 1360 is configured to produce an electrical output corresponding to a load, for example an anatomical load, that the rod is subjected to. The electrical output generated by the rod 1360 is transmitted to the plurality of screws 1352 and, through the screws, into the vertebrae.

Figure 14:
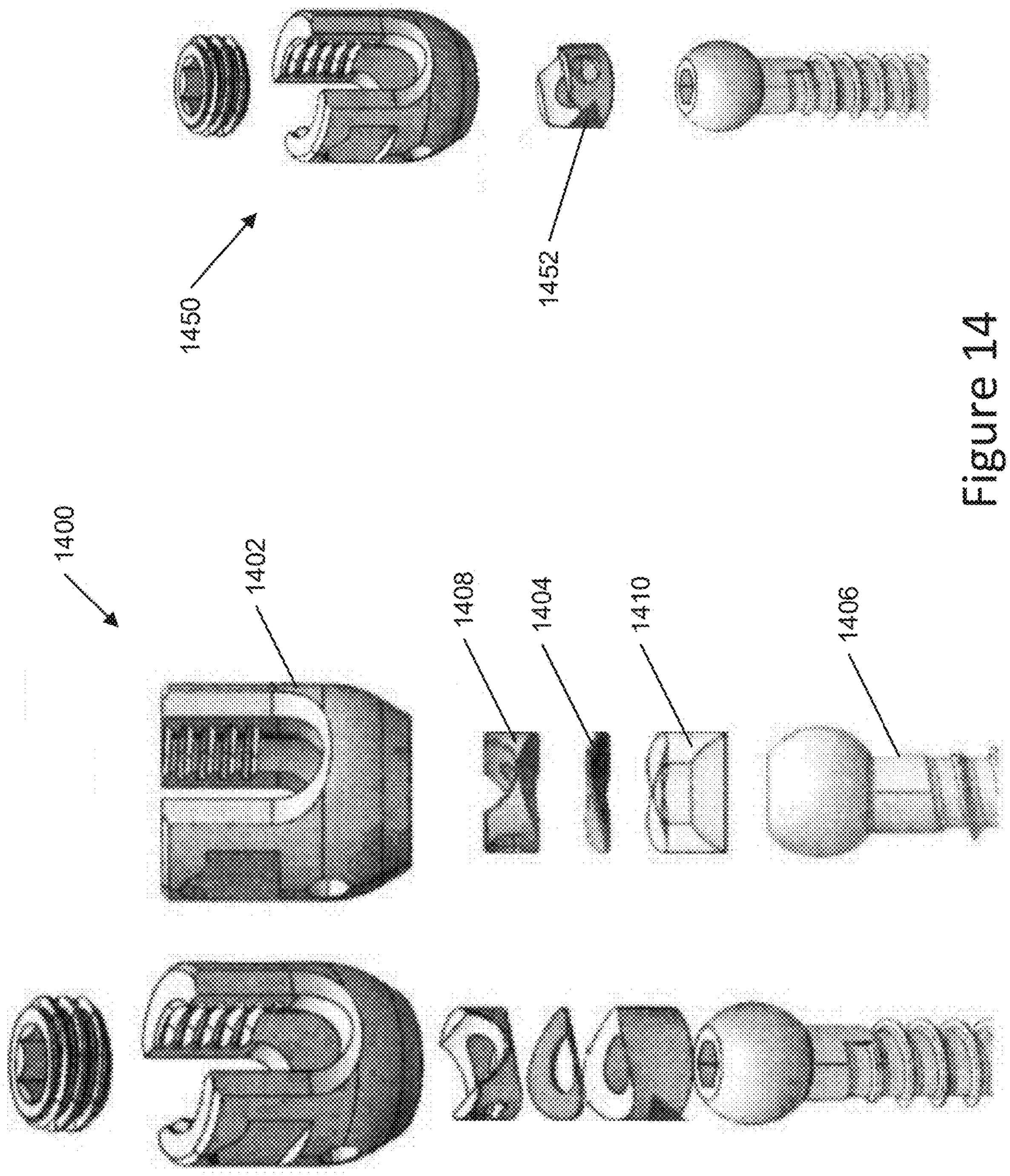
FIG. 14 shows a pedicle screw assembly in accordance with an embodiment of the invention.

FIG. 14 shows a pedicle screw assembly in accordance with an embodiment of the present invention. Pedicle screw 1400 is configured to be screwed into a vertebra. The pedicle screw 1400 has a head 1402, a rod saddle 1408, a screw head saddle 1410, and a body 1406. The head 1402 is coupled to the body 1406 by the rod saddle 1408 and screw head saddle 1410. The body 1406 is configured to be screwed into the vertebra. The head 1402 also includes an opening by which the screw 1400 can be attached to a rod, as shown above in FIG. 13B. A piezoelectric layer 1404 is disposed between the rod saddle 1408 and the screw head saddle 1410. The piezoelectric layer 1404 may be made from PVDF, or other piezoelectric material, and is configured to produce an electrical output corresponding to a load, for example an anatomical load, that the pedicle screw is subjected to. The neck and body of the pedicle screw 1400 may also be made from a conductive material so that the electrical output from the piezoelectric layer 1404 is transmitted through screw head saddle and body of the pedicle screw 1400 into the vertebra. The head 1402 may also be made from a conductive material and is electrically coupled to the rod saddle so that the electrical output from the piezoelectric layer 1404 is transmitted through the rod saddle and head into an attached rod. The rod saddle 1408 has a contoured underside to actuate the electrical output of the piezoelectric layer 1404. Similarly, the screw head saddle 1410 has a contoured top surface to actuate the electrical output of the piezoelectric layer 1404. FIG. 14 also shows a standard pedicle screw assembly 1450, which comprises a standard rod saddle 1452.

Figure 15:
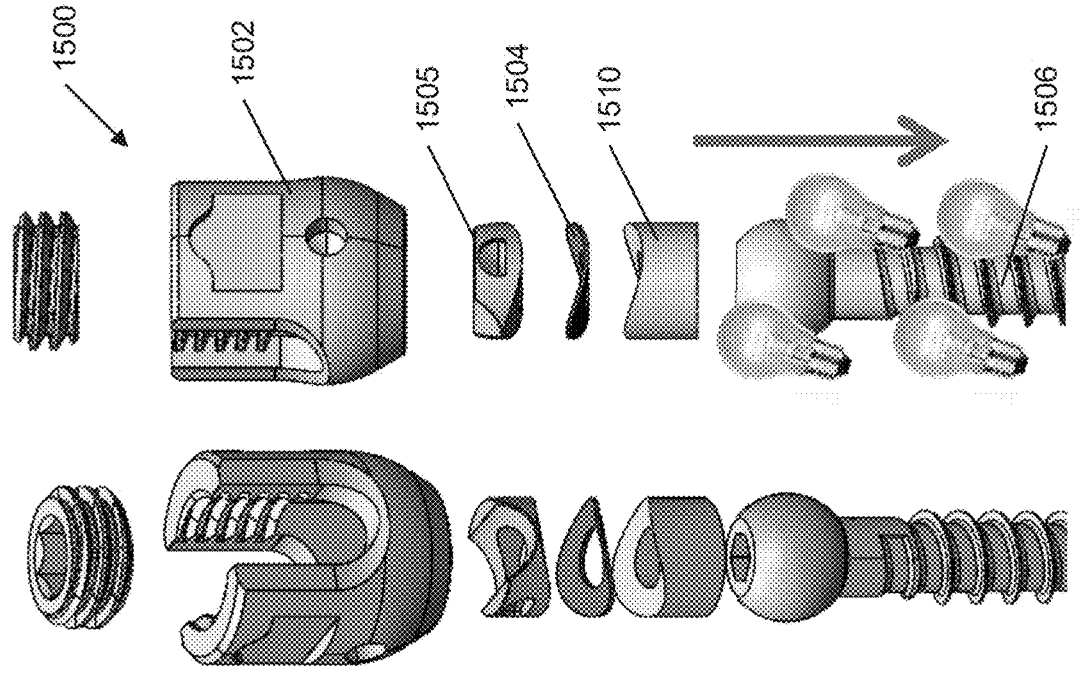
FIG. 15 shows a pedicle screw assembly in accordance with an embodiment of the invention.

FIG. 15 shows a pedicle screw assembly in accordance with an embodiment of the present invention. Pedicle screw 1500 has a head 1502, a body 1506, a screw head saddle 1510, and a piezoelectric layer 1504. These elements are understood to be substantially the same as what is shown and described above with reference to FIG. 14. In addition, pedicle screw 1500 has an insulator 1505. The insulator is located between piezoelectric layer 1504 and head 1502 and electrically insulates the head 1502 from the piezoelectric layer 1504. Therefore, the electrical output from the piezoelectric layer 1504 is only transmitted to the body of the pedicle screw, but not to the head 1502 or to any rod attached to the head.

Figure 16:
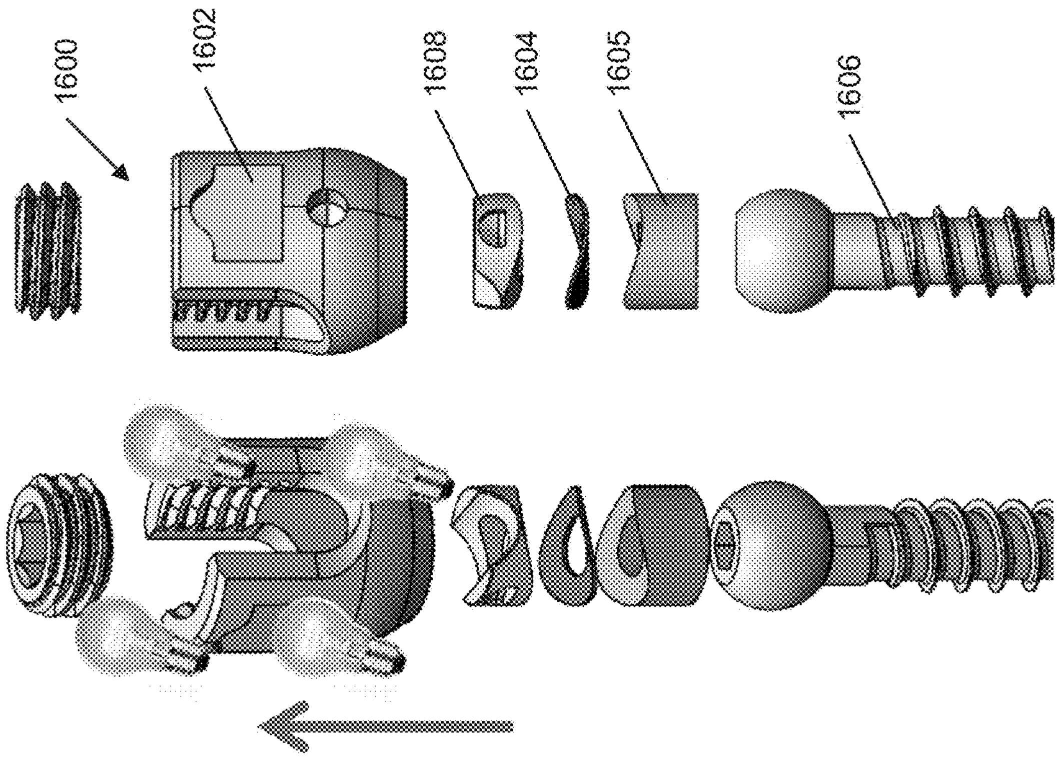
FIG. 16 shows a pedicle screw assembly in accordance with an embodiment of the invention.

FIG. 16 shows a pedicle screw assembly in accordance with an embodiment of the present invention. Pedicle screw 1600 has a head 1602, a body 1606, a rod saddle 1608, and a piezoelectric layer 1604. These elements are understood to be substantially the same as what is shown and described above with reference to FIG. 14. In addition, pedicle screw 1600 has an insulator 1605. The insulator is located between piezoelectric layer 1604 and body 1606 and electrically insulates the body 1606 from the piezoelectric layer 1604. Therefore, the electrical output from the piezoelectric layer 1604 is only transmitted to the head 1602 of the pedicle screw, and to any rod attached to the head, but not to the body 1606 or the vertebra.

Figure 17:
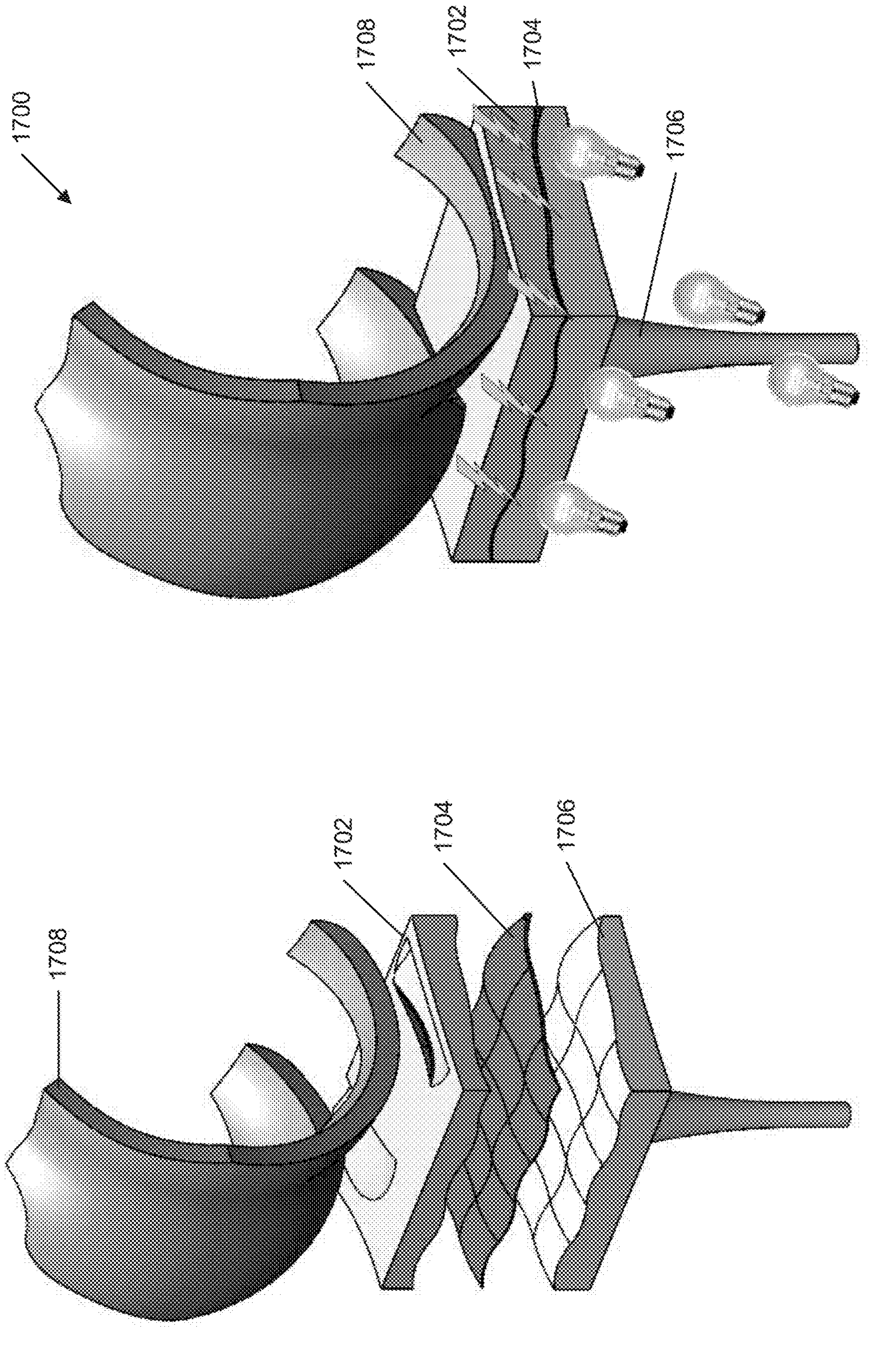
FIG. 17 shows a joint implant assembly in accordance with an embodiment of the invention.

FIG. 17 shows a joint implant assembly 1700 in accordance with an embodiment of the present invention. While a knee implant is shown and described, it is expressly contemplated that the implant assembly 1700 can be configured for other joints, such has a hip joint or an ankle joint. The knee joint implant assembly 1700 in this example includes a femoral implant 1708 and a tibial implant that has a platform 1706. The tibial implant also includes a piezoelectric layer 1704 and a friction surface 1702. The piezoelectric layer 1704 is made from PVDF or other piezoelectric material, and is configured to produce an electrical output corresponding to a load, for example an anatomical load, that the joint implant assembly 1700 is subjected to. The tibial implant onto which the piezoelectric layer 1704 is disposed may be made from a conductive material, such as titanium, that transmits the electrical output into the bone. The underside of the friction surface 1702 and/or the surface of the tibia platform 1706 are contoured to actuate the electrical output of the piezoelectric layer 1704.

Figure 18:
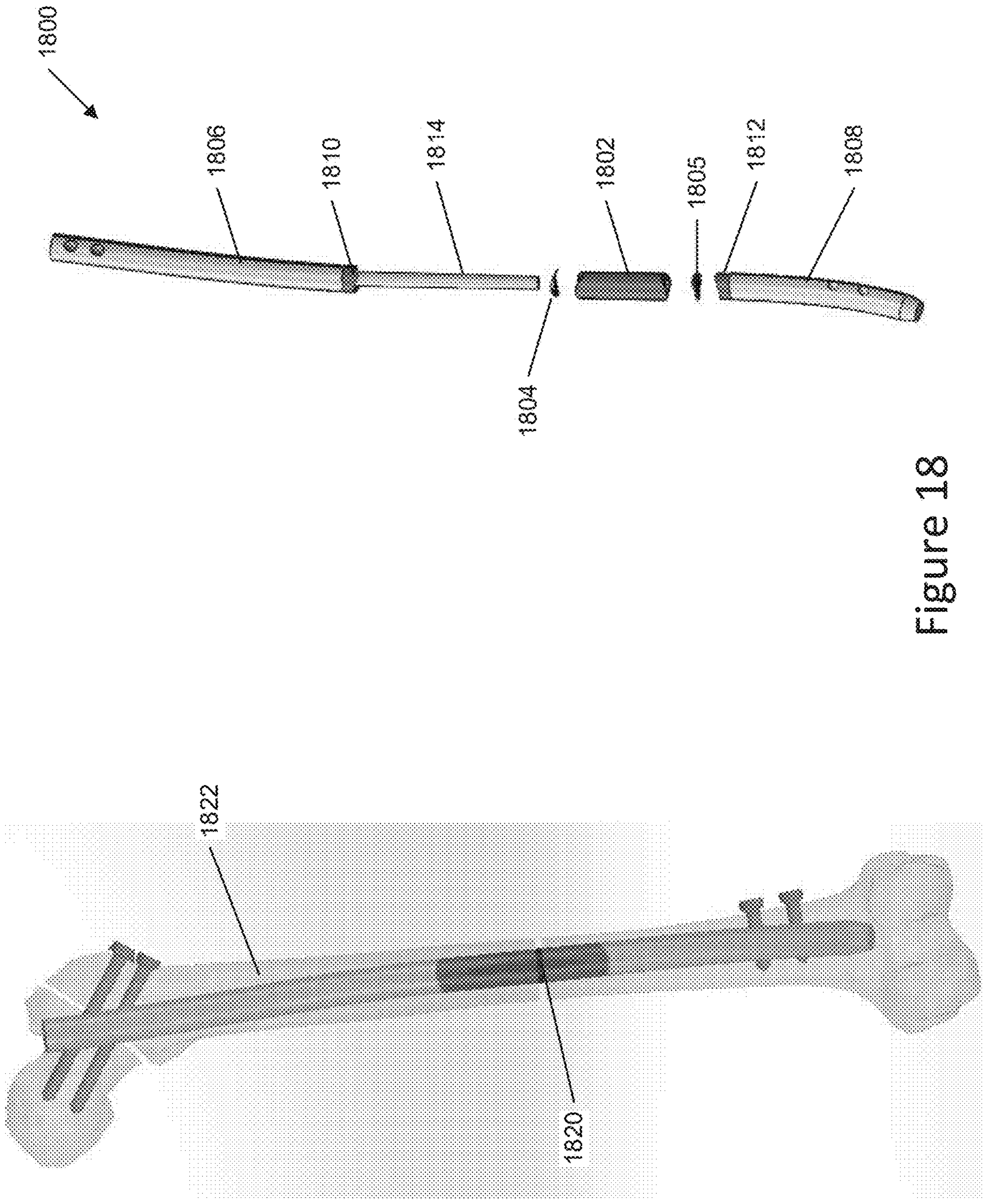
FIG. 18 shows an intermedullary nail assembly in accordance with an embodiment of the invention.

FIG. 18 shows an intramedullary nail assembly in accordance with an embodiment of the present invention. The intramedullary nail assembly 1800 includes an upper shaft 1806 and a lower shaft 1808. The upper and lower shafts may be made from titanium or other suitable implant material. The upper shaft 1806 includes a pin 1814 configured to connect the upper shaft to the lower shaft. The intramedullary nail assembly 1800 further includes an electrical conductor 1802 disposed between the upper shaft and the lower shaft. The electrical conductor 1802 is advantageously positioned across a fracture 1820 in the bone 1822 that the intramedullary nail assembly is implanted into. A first piezoelectric ring 1804 is disposed between the electrical conductor 1802 and the upper shaft 1806, and a second piezoelectric ring 1805 is disposed between the electrical conductor 1802 and the lower shaft 1808. The first and second piezoelectric rings may be manufactured from PVDF, or other piezoelectric material, and are configured to produce an electrical output corresponding to a load, for example an anatomical load, that the respective ring is subjected to. The electrical output of the first and second piezoelectric rings is transmitted through the electrical conductor 1802 to the fractured bone 1822 in the area of the fracture 1820 to promote bone growth and healing of the fracture. The upper shaft 1806 also has an upper insulated cap 1810 that is contoured to deform the first piezoelectric ring 1804 and actuate its electrical output. The upper insulated cap 1810 is further configured to insulate the upper shaft 1806 from the electrical conductor 1802. The lower shaft 1808 similarly has a lower insulated cap 1812 that is contoured to deform the second piezoelectric ring 1805 and actuate its electrical output. The lower insulated cap 1812 is further configured to insulate the lower shaft 1808 from the electrical conductor 1802.

Figure 19:
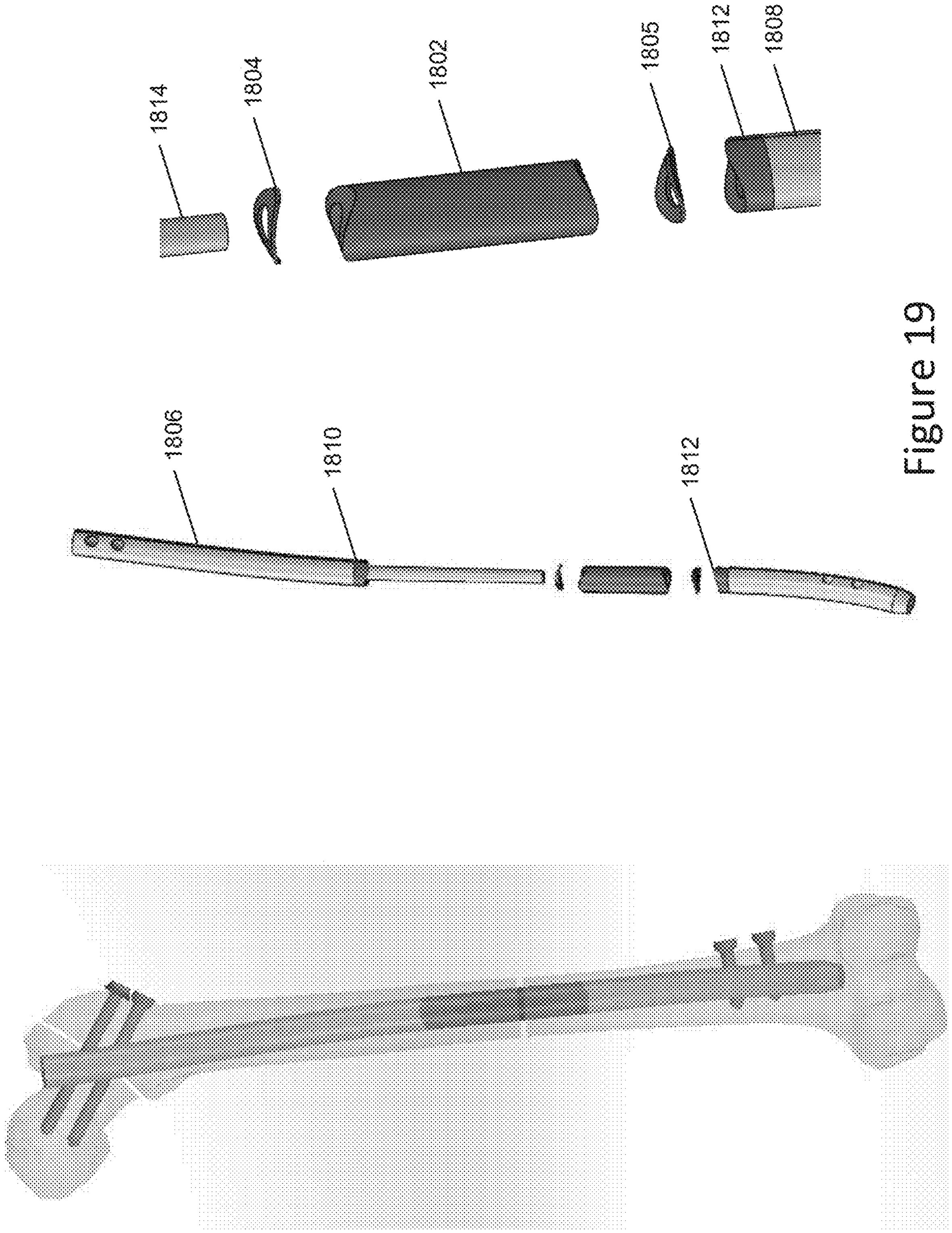
FIG. 19 shows an intermedullary nail assembly in accordance with an embodiment of the invention.

FIG. 19 shows another view of intramedullary nail assembly 1800. It can be seen that the first and second piezoelectric rings 1804 and 1805 adapt to the contours of upper and lower insulated caps 1810 and 1812, respectively.

Figure 20:
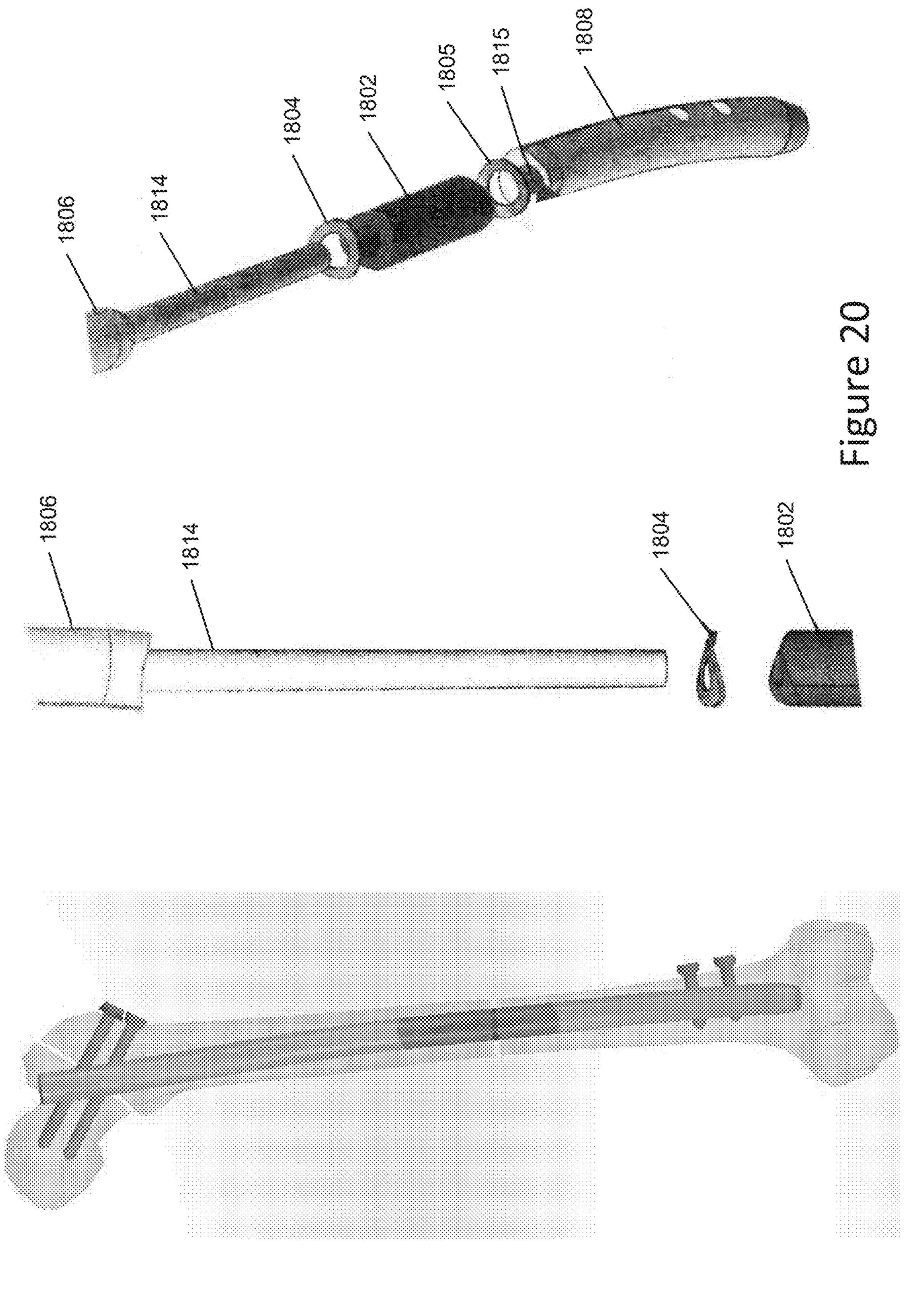
FIG. 20 shows an intermedullary nail assembly in accordance with an embodiment of the invention.

FIG. 20 is another view of intramedullary nail assembly 1800. The pin 1814 from upper shaft 1806 is inserted into a pin hole 1815 in lower shaft 1808 to connect the upper shaft to the lower shaft. The electrical conductor 1802 sits in between the upper shaft 1806 and 1808. The electrical conductor 1802 also has a pin hole configured to receive the pin 1814 from the upper shaft. In other words, the pin 1814 extends from the upper shaft 1806 through the electrical conductor 1802 into the lower shaft 1808. The first piezoelectric ring 1804 is arranged between the upper shaft (and its upper insulated cap) and the electrical conductor. The second piezoelectric ring 1805 is arranged between the lower shaft (and its lower insulated cap) and the electrical conductor.

Figure 21:
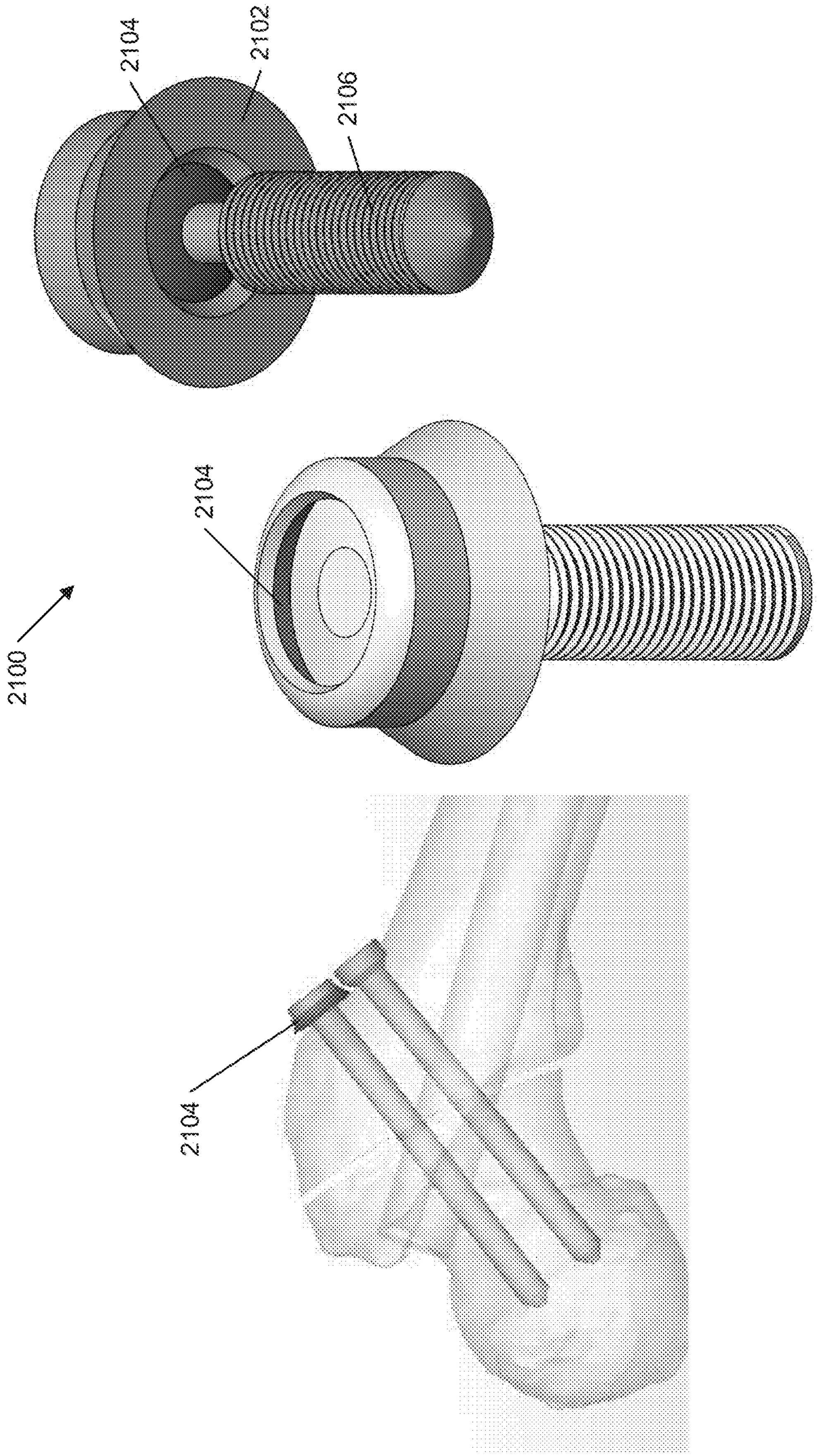
FIG. 21 shows an intermedullary screw assembly in accordance with an embodiment of the invention.

FIG. 21 shows a bone screw assembly in accordance with an embodiment of the present invention. Bone screw 2100 includes a screw head 2102 connected to a screw body 2106. The head 2102 includes a washer 2104. The washer 2104 may be manufactured from a piezoelectric material, or it may include a piezoelectric layer disposed on the washer. The piezoelectric material may be PVDF, or other piezoelectric material, and is configured to produce an electrical output corresponding to a load, for example an anatomical load, that the washer is subjected to. The electrical output generated by the piezoelectric material is transmitted through the screw body 2106 into the bone. The screw head 2102 may be smooth, or it may have undulations to enhance the electrical output generated by the piezoelectric material.

Figure 22:
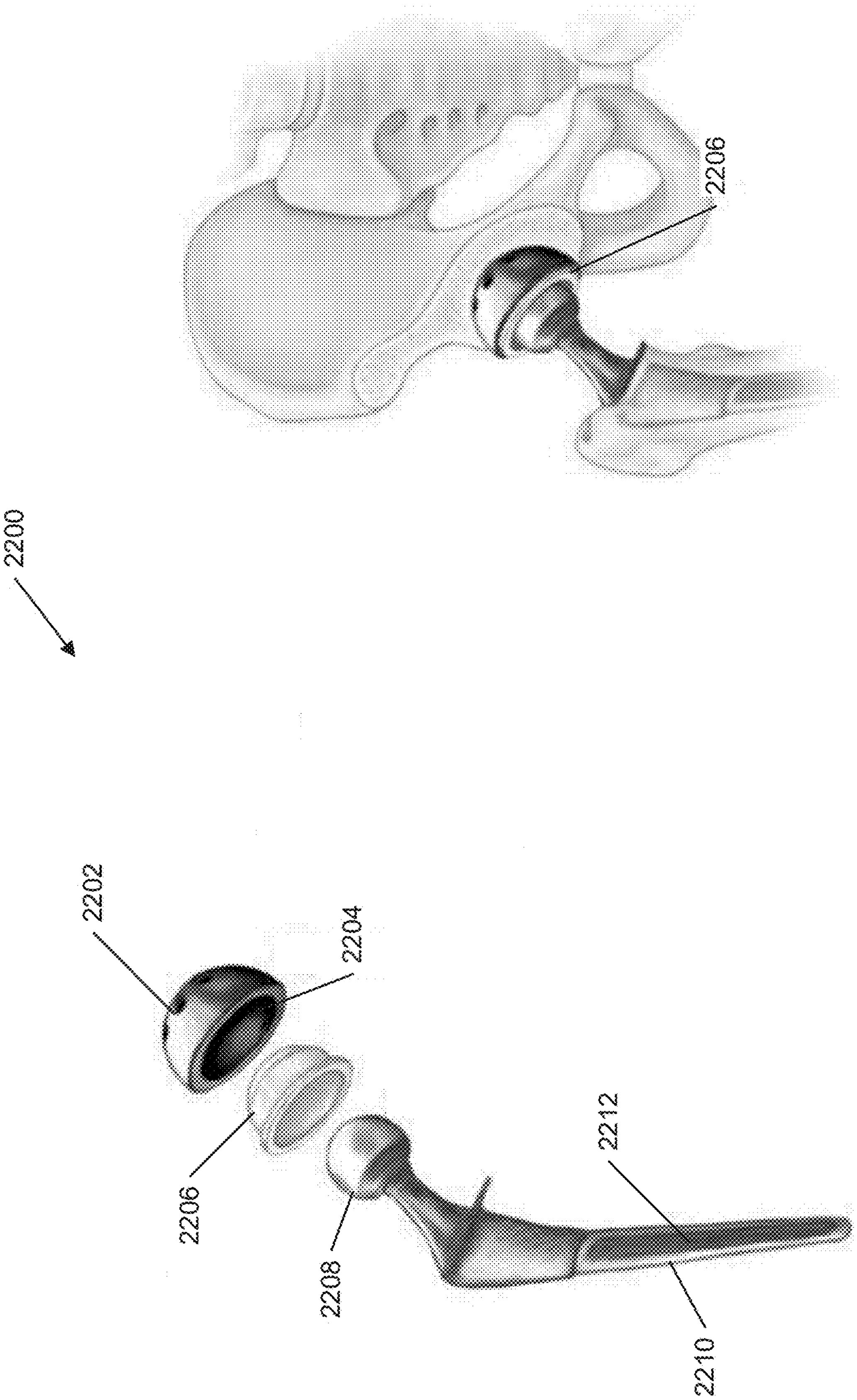
FIG. 22 shows a hip replacement assembly in accordance with an embodiment of the invention.

FIG. 22 shows a hip replacement assembly in accordance with an embodiment of the present invention. Hip replacement assembly 2200 includes an acetabular component 2202 an insulating liner 2206 which is, for example, made from plastic, a femoral head 2208, and a femoral stem 2210. The acetabular component 2202 is configured to be attached to the acetabulum of a hip bone and includes an acetabular piezoelectric layer 2204 which is disposed on an articulating surface of the acetabular component 2202 facing away from the hip bone. This arrangement allows for the femoral head 2208 to generate a load on the articulating surface of the acetabular component, and thereby the acetabular piezoelectric layer, when the hip replacement assembly 2200 is implanted. The acetabular piezoelectric layer 2204 is made from PVDF, or other piezoelectric material, and is configured to produce an electrical output corresponding to a load, for example an anatomical load, that the hip replacement assembly 2200 is subjected to. The insulating liner 2206 is then disposed on the acetabular piezoelectric layer 2204. The acetabular component 2202 is made from a conductive material so that the electrical output generated by the acetabular piezoelectric layer 2204 is transmitted into the hip bone. The insulating layer 2206 may instead be a piezoelectric layer configured to generate an electrical output corresponding to a load, such as an anatomical load, that the hip replacement is subjected to.

The femoral head 2208 is rigidly coupled to the femoral stem 2210. The femoral stem 2210 is configured to be implanted into a femur and includes a femoral piezoelectric layer 2212. The femoral piezoelectric layer 2212 is made from PVDF, or other piezoelectric material, and is configured to produce an electrical output corresponding to a load, for example an anatomical load, that the hip replacement assembly 2200 is subjected to. The femoral stem 2210 is made from a conductive material so that the electric output generated by the femoral piezoelectric layer 2212 is transmitted into the femur.

Figure 23:
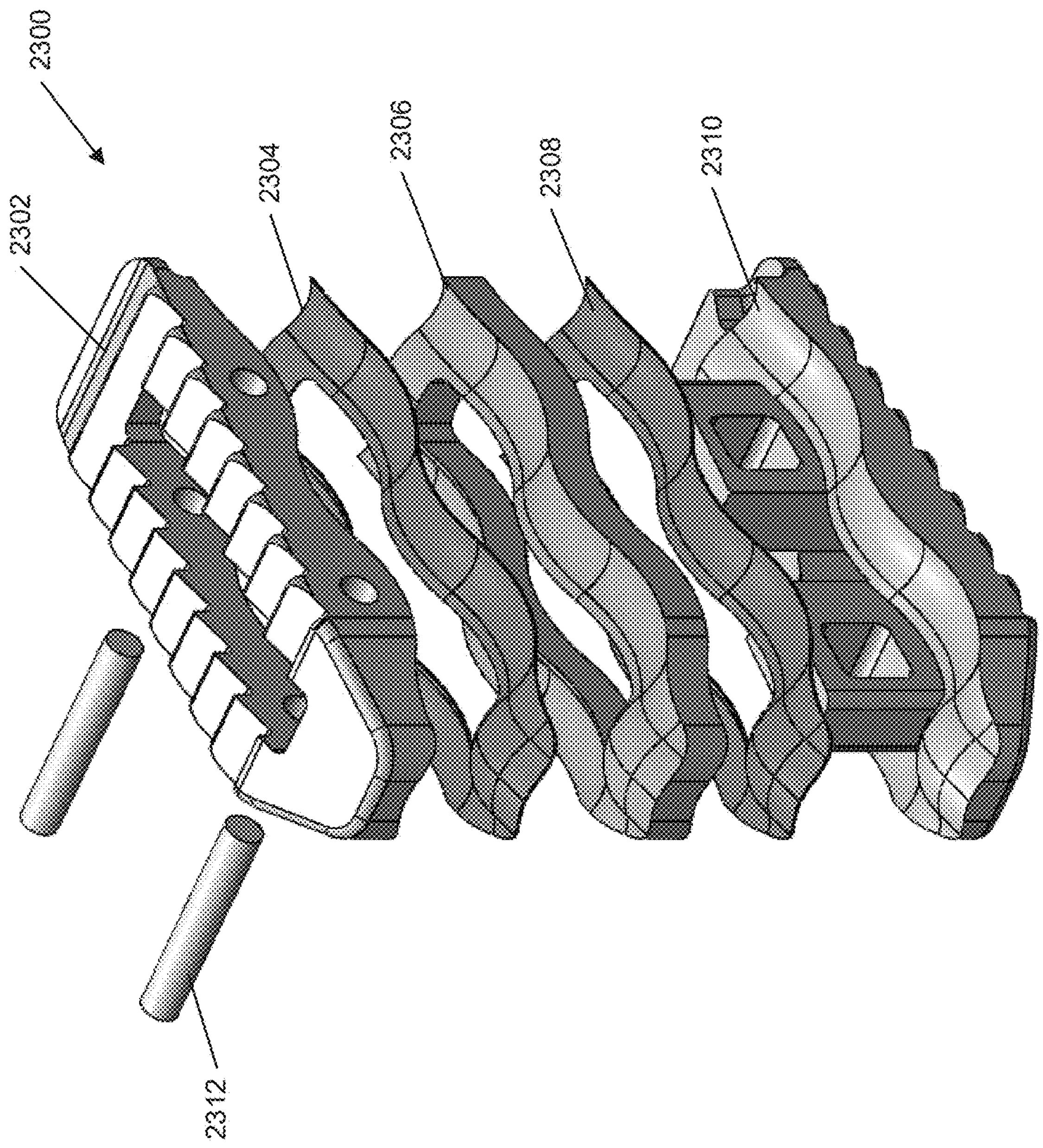
FIG. 23 shows a bone spacer assembly in accordance with an embodiment of the invention.

FIG. 23 shows a bone spacer assembly, which may also be a bone void filler, in accordance with an embodiment of the present invention. Bone void fillers may be used in treatment of bone defects or alignment, including those in the feet, ankles, hands, wrists, spine, and others. Bone spacer assembly 2300 includes a top endplate 2302 and a bottom endplate 2310. The top endplate and bottom endplate may be manufactured from titanium. The top endplate and bottom endplate may also be 3D-printed. The bone spacer assembly 2300 further includes a first piezoelectric layer 2304 and a second piezoelectric layer 2308. The first and second piezoelectric layers may be made from PVDF, or other piezoelectric material, and are configured to produce an electrical output corresponding to a load, for example an anatomical load, that the bone spacer assembly 2300 is subjected to. The bone spacer assembly 2300 also includes an insulator 2306, which may be made from polyether ether ketone (PEEK). The bone spacer assembly 2300 is assembled in that that second piezoelectric layer 2308 is disposed on the bottom endplate 2310, the insulator 2306 is disposed on the second piezoelectric layer 2308, the first piezoelectric layer 2304 is disposed on the insulator 2306, and the top endplate 2302 is disposed on the first piezoelectric layer 2304. A set of assembly pins 2312 holds the components of the bone spacer assembly 2300 together.

The insulator 2306 has contoured top and bottom surfaces to actuate the output of the piezoelectric layers. The top endplate 2302 has a contoured bottom surface that matches the top surface of the insulator 2306. The bottom endplate 2310 has a contoured top surfaces that matches the bottom surface of the insulator 2306. The piezoelectric layers 2304 and 2308 are sandwiched between the contoured surfaces. The contouring deforms the piezoelectric layers to increase strain under compressive load to increase electric output.

Instead of having a insulator and two piezoelectric layers sandwiched between the top and bottom endplates, as described above, it expressly contemplated that only a single piezoelectric layer may be sandwiched between the top and bottom endplates. In this embodiment, the contoured bottom surface of the top endplate matches the contoured top surface of the bottom endplate. The piezoelectric layer is then sandwiched between the contoured surfaces, which deform the piezoelectric layer to increase strain under compressive load to increase electric output.

Figure 24:
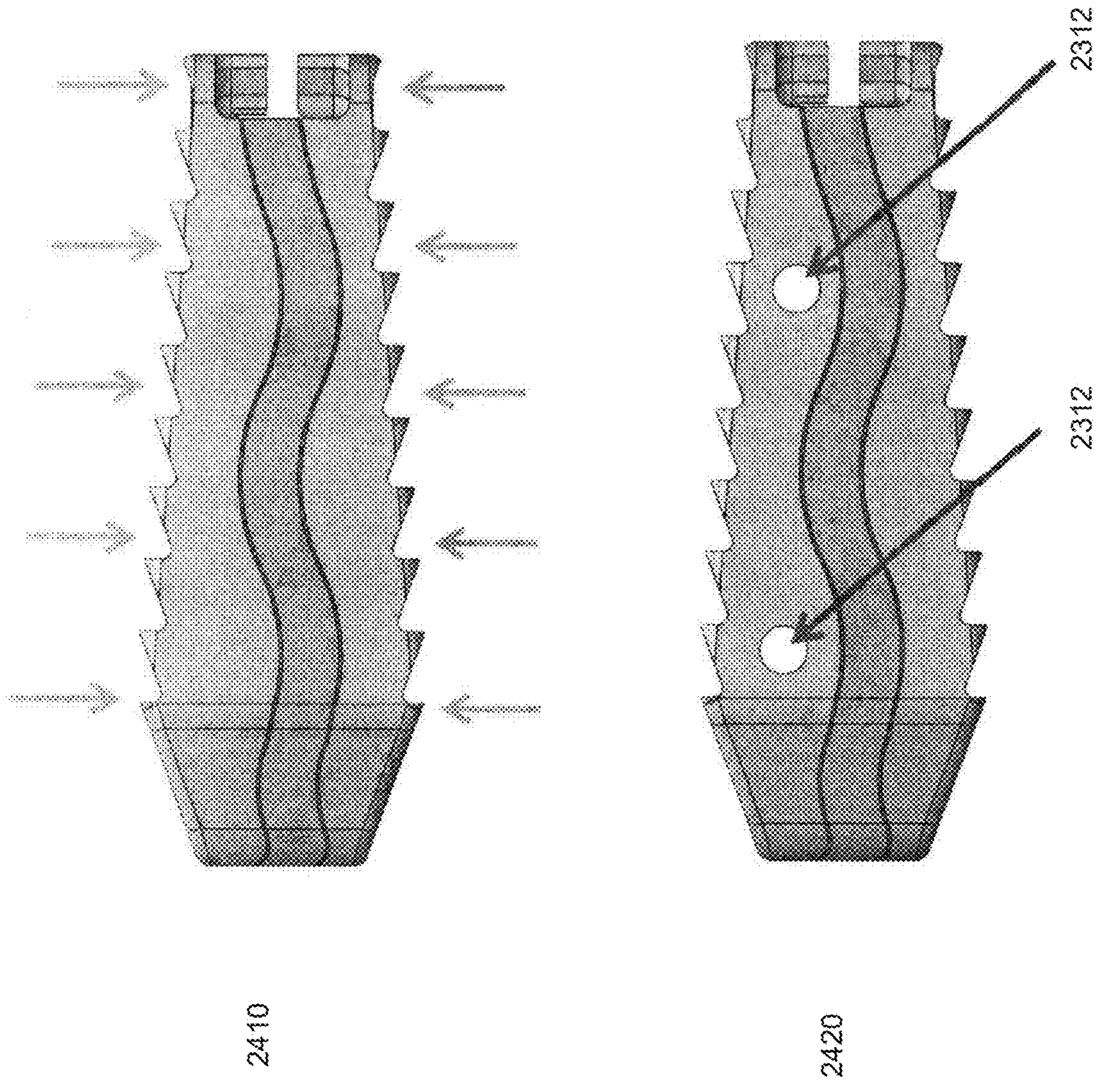
FIG. 24 shows a method to assemble a bone spacer assembly in accordance with an embodiment of the invention.
Figure 25:
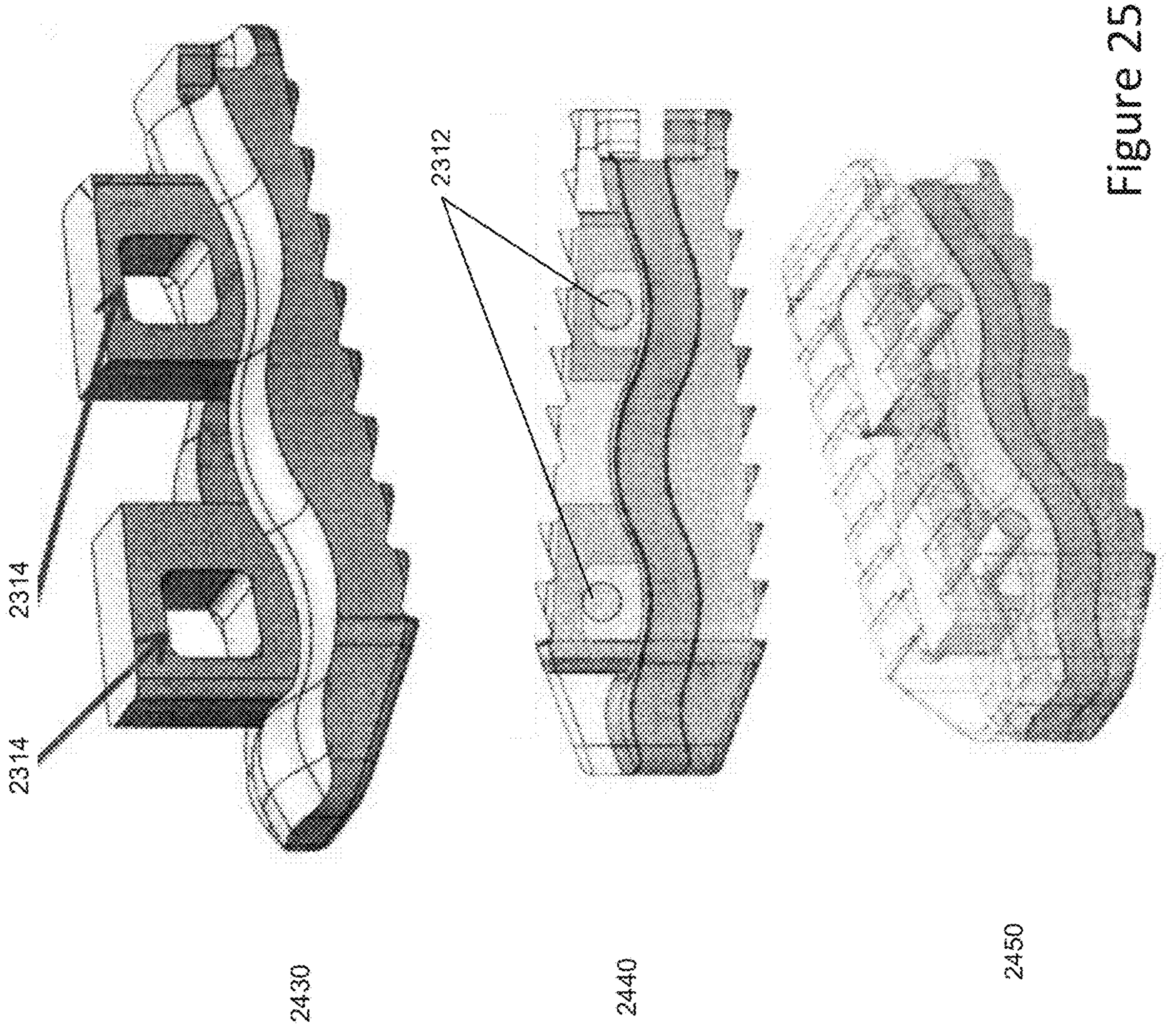
FIG. 25 shows a method to assemble a bone spacer assembly in accordance with an embodiment of the invention.

FIGS. 24 and 25 show a method to assemble a bone spacer assembly (or bone void filler), such as bone spacer assembly 2300, in accordance with an embodiment of the present invention. In step 2410, top and bottom endplates are 3D-printed without pin holes. The endplates, piezoelectric layers, and insulator are then assembled as shown above with reference to FIG. 23. Pressure is applied to the top and the bottom of the bone spacer assembly to conform the piezoelectric layers to the internal contours.

In step 2420, precision holes for the assembly pins 2312 are drilled which the assembly is still compressed. Drilling the holes while the assembly is compressed ensures that the holes are drilled through both the top and bottom endplates to guarantee perfect alignment. In step 2430, the assembly is disassembled and the holes of the bottom endplate are expanded to result in expanded holes 2314. The top border of expanded holes 2314 is maintained at the same vertical position as the drilled hole to ensure that the bone spacer assembly stays in the compressed state when it is reassembled.

In step 2440, the bone spacer assembly is reassembled and compressed to line up the drilled holes in the top endplate with the expanded holes in the bottom endplate. In step 2450, pins 2312 are inserted to keep the bone spacer assembly in the compressed state. The expanded holes 2314 ensure that the bone spacer assembly 2300 can be compressed even more when subjected to a load to allow the first and second piezoelectric layers to generate an electrical output.

Figure 26:
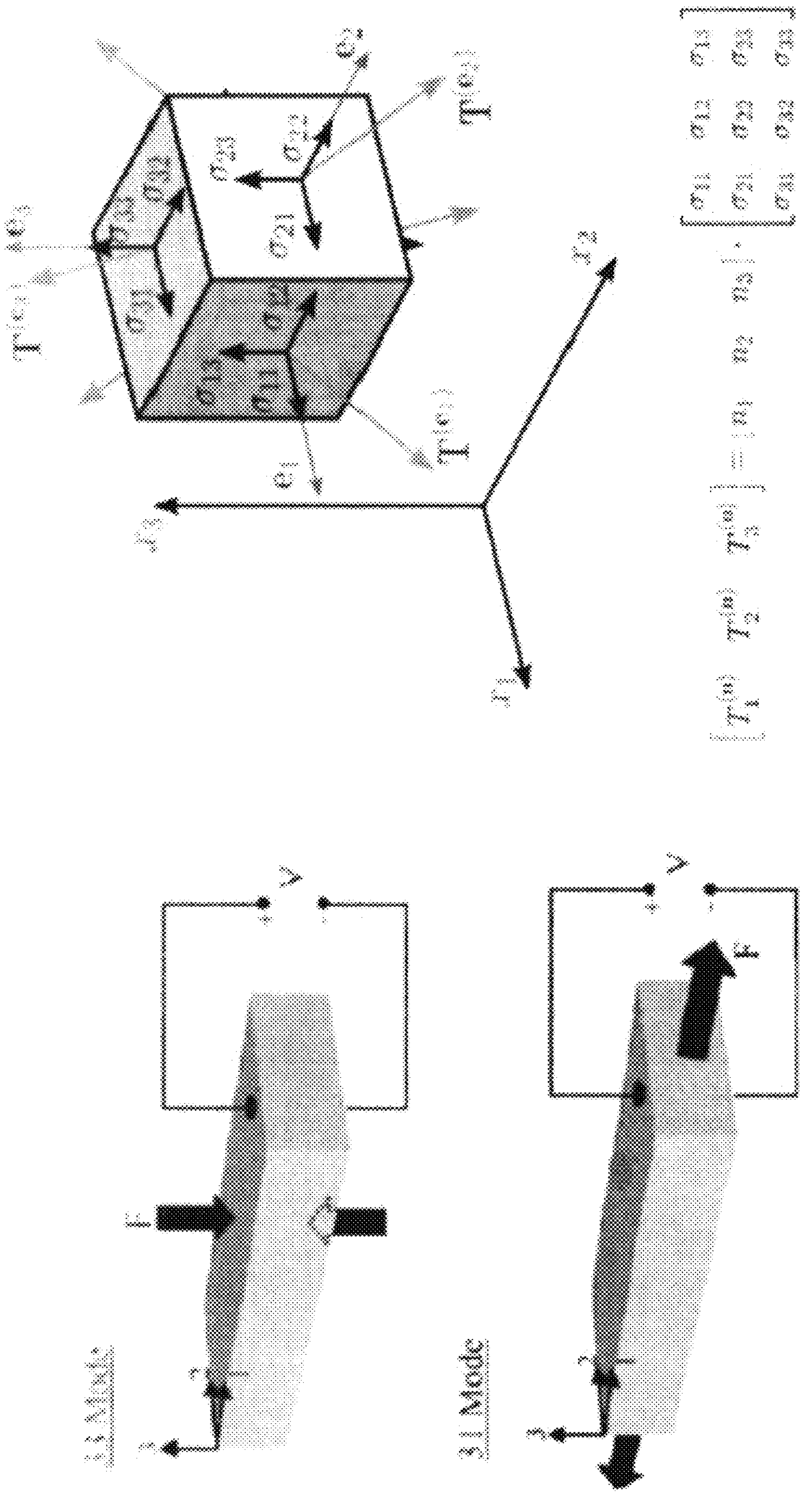
FIG. 26 shows a mechanism to activate PVDF in accordance with an embodiment of the invention.

FIG. 26 shows a mechanism to activate PVDF, or other piezoelectric material, in accordance with an embodiment of the present invention. As describe above, piezoelectric materials are known to have varying levels of response depending on the direction and magnitude of the force applied. Stress is commonly broken into directional components and described by a 3 by 3 "Cauchy stress tensor" matrix, where d11, d22, and d33 are axial compression along the x, y, and z axes respectively.

The matrix entries in the top right and bottom left corners of the matrix are d31 and d13, and represent planar shear stress. An advantageous mechanism to activate a piezoelectric material is to transfer compressive load into the d31 mode of displacement to increase electrical output. For certain piezoelectric materials, such as the treated PVDF in several embodiments herein, the piezoelectric constant for d31 may by more than double that of the piezoelectric constant in other directions. This increase in magnitude of the electrical signal for a given loading scenario is highly desirable and creates a meaningful impact on the performance of the end product.

Figure 27:
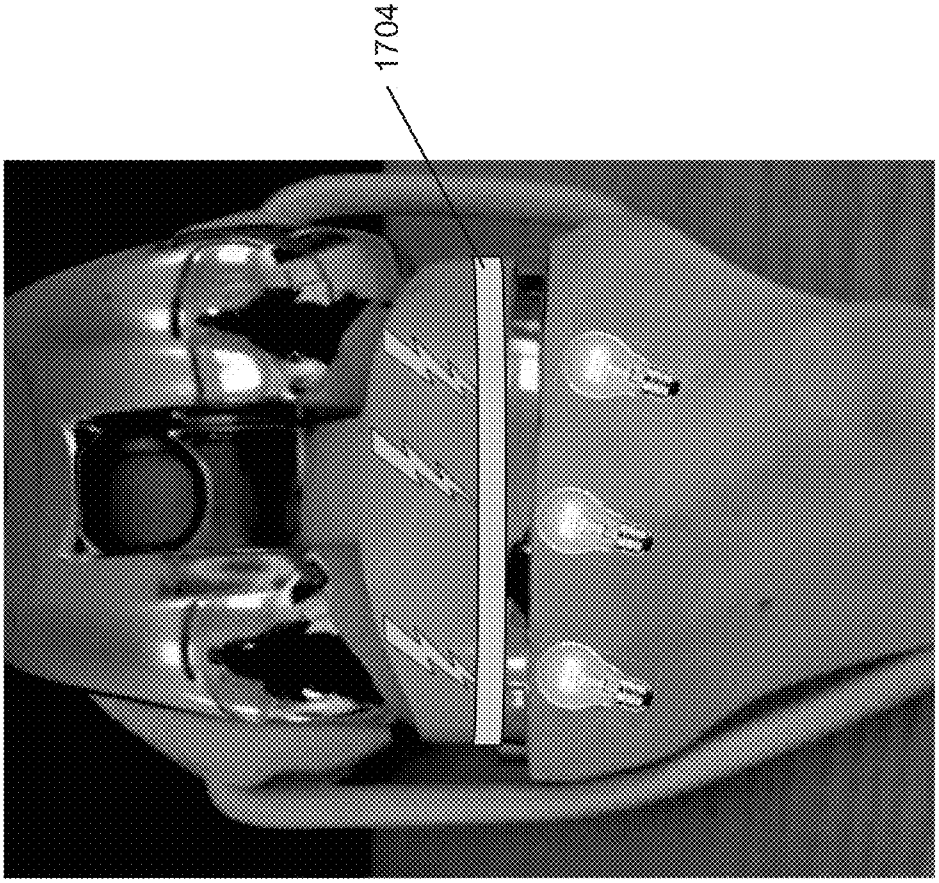
FIG. 27 shows a knee implant assembly in accordance with an embodiment of the invention.

FIG. 27 shows an embodiment of a piezoelectric knee implant, such as the one shown and described in relation to FIG. 17. Piezoelectric layer 1704 generates an electric output which is received by one or more bones.

Figure 28:
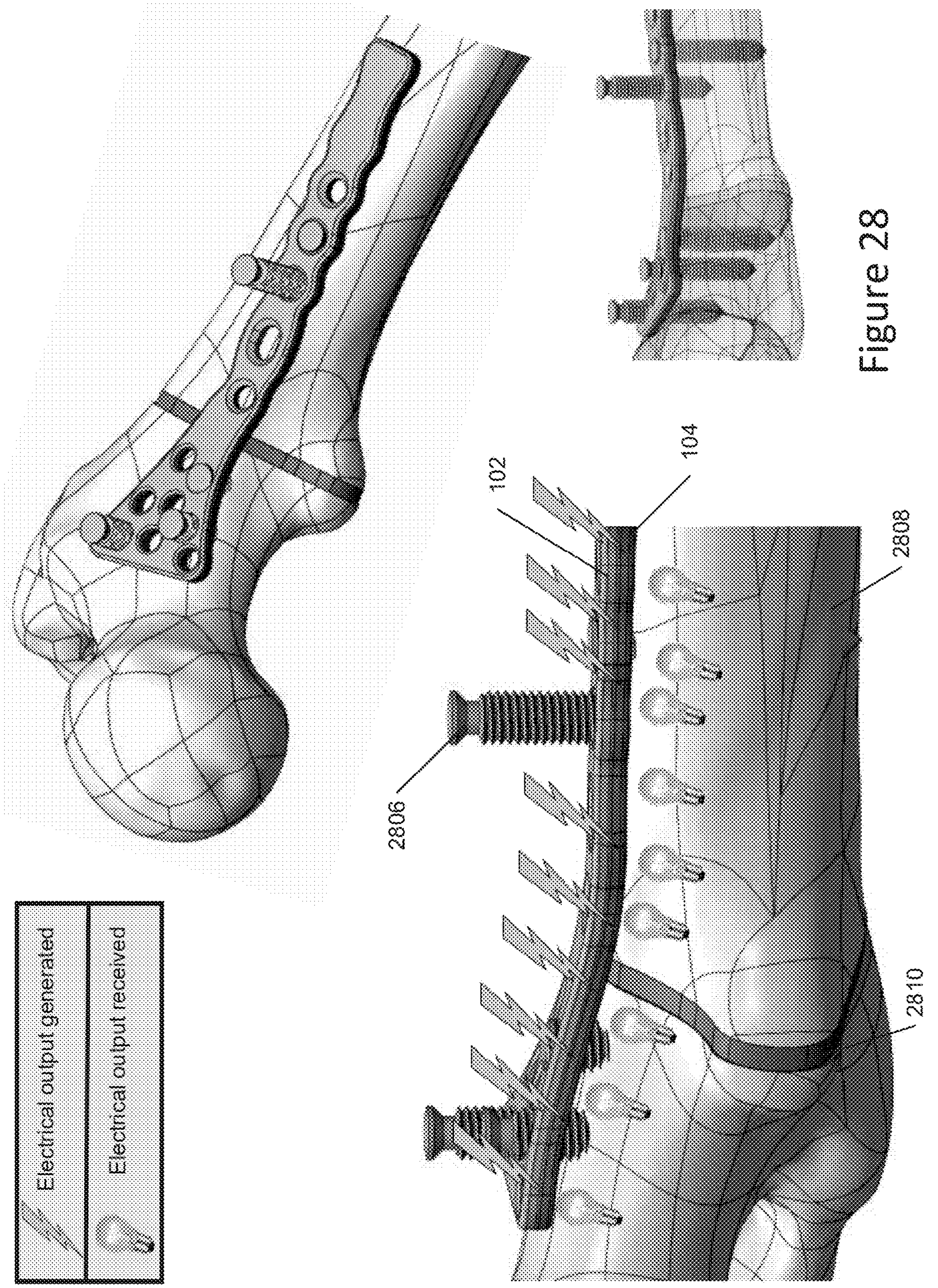
FIG. 28 shows an implant assembly in accordance with an embodiment of the invention.

FIG. 28 shows an embodiment of a piezoelectric implant assembly, such as the one shown and described in relation to FIG. 1. Bone plate 102 is fitted with a piezoelectric cover 104, and affixed to bone 2808 via screws 2806, spanning fracture 2810. Force applied by the screws, and optionally other forces, cause the piezoelectric cover 104 to generate an electrical output (shown by the lightning bolt icons), which is received by the bone 2808 (shown by the light bulb icons).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A kit to form an orthopedic implant assembly, the kit comprising:

a bone plate having a distal surface configured to contact a fractured bone and a proximal surface opposite the distal surface;

a first component having a conical-frustum-shape with a continuous taper between a distal side and a proximal side and including a piezoelectric material and having a first surface that, when in the orthopedic implant assembly, is non-planar; and a second component having a second surface, the second surface being non-planar, wherein, when in the orthopedic implant assembly, the first component is configured to be between the bone plate and the second component and the first surface conforms to and is adjacent to the second surface.

2. The kit of claim 1, wherein the first surface and the second surface each include component surfaces that have an orientation of a 30 degree angle to a 60 degree angle relative to a vertical axis.

3. The kit of claim 1, wherein:

the first component includes a plurality of rings, and the first surface comprises concave-conical-frustum-shaped ring surfaces of respective ones of the plurality of rings;

the second component includes a plurality of fasteners, and the second surface comprises convex-conical-frustum-shaped bearing surfaces at an underside of heads of respective ones of the plurality of fasteners, individual ones of the concave-conical-frustum-shaped ring surfaces conforming to and adjacent to respective corresponding ones of the convex-conical-frustum-shaped bearing surfaces of the plurality of fasteners;

wherein the bone plate defines a plurality of openings extending therethrough such that the plurality of fasteners extend, when in the orthopedic implant assembly, through the plurality of openings to attach the orthopedic implant assembly to a bone, respective ones of the plurality of rings to be, when in the orthopedic implant assembly, between respective ones of the plurality of fasteners on one hand, and the bone plate on another hand.

4. The kit of claim 3, wherein:

the plurality of fasteners include a plurality of screws; and the plurality of openings comprise a plurality of threaded openings, the plurality of screws configured to extend through and engage threads of corresponding ones of the plurality of threaded openings when in the orthopedic implant assembly.

5. The kit of claim 4, wherein the plurality of screws are lag screws.

6. The kit of claim 4, wherein some of the plurality of screws have lengths that are different from lengths of other ones of the plurality of screws.

7. The kit of claim 3, wherein:

respective ones of the plurality of rings include convex-conical-frustum-shaped ring surfaces opposite the concave-conical-frustum-shaped ring surfaces; and the bone plate defines, at entry regions of respective ones of the plurality of openings thereof, respective concave-conical-frustum-shaped bone plate surfaces that are to receive, when in the orthopedic implant assembly, corresponding ones of the convex-conical-frustum-shaped ring surfaces.

8. The kit of claim 1, wherein the piezoelectric material includes at least one of polyvinylidene fluoride or polyvinylidene difluoride (PVDF).

9. The kit of claim 1, wherein a material of the bone plate and a material of the second component is selected from the group consisting of an electrically conductive material, an electrically non-conductive material, and combinations thereof.

10. The kit of claim 1, wherein the bone plate, the first component and the second component are configured such that the bone plate and the second component are to cause at least one of a compressive force or a shear force on the first component.

11. The kit of claim 10, wherein the at least one of the compressive force or the shear force are to be distributed unevenly throughout the first component.

12. The kit of claim 1, wherein the second component has an outer surface, and wherein the first component is configured to produce, for the orthopedic implant assembly, an electrical output corresponding to a load applied to the outer surface of the bone plate and to the outer surface of the second component.

13. An orthopedic implant assembly comprising:

a bone plate having a distal surface configured to contact a fractured bone, a proximal surface opposite the distal surface, and one or more openings extending between the proximal surface and the distal surface;

a first component comprising one or more rings comprising a piezoelectric material and having a frustoconical shape with a continuous taper between a proximal side and a distal side and a first surface; and a second component comprising one or more fasteners having a second surface, wherein the one or more rings are configured to be disposed in the one or more openings between the bone plate and the one or more fasteners and the first surface is configured to be adjacent to and conform to the second surface.

14. The orthopedic implant assembly of claim 13, wherein the first surface and the second surface each include component surfaces that have an orientation of a 30 degree angle to a 60 degree angle relative to a vertical axis.

15. The orthopedic implant assembly of claim 13, wherein:

the one or more rings comprises a plurality of rings, and the first surface comprises concave-conical-frustum-shaped ring surfaces of respective ones of the plurality of rings; and the one or more fasteners comprises a plurality of fasteners, and the second surface comprises convex-conical-frustum-shaped bearing surfaces at an underside of heads of respective ones of the plurality of fasteners, individual ones of the concave-conical-frustum-shaped ring surfaces conforming to and adjacent to respective corresponding ones of the convex-conical-frustum-shaped bearing surfaces of the plurality of fasteners.

16. The orthopedic implant assembly of claim 15, wherein:

the plurality of fasteners include a plurality of screws; and the one or more openings comprises a plurality of threaded openings, the plurality of screws extending through and engaging threads of corresponding ones of the plurality of threaded openings.

17. The orthopedic implant assembly of claim 16, wherein the plurality of screws are lag screws.

18. The orthopedic implant assembly of claim 16, wherein some of the plurality of screws have lengths that are different from lengths of other ones of the plurality of screws.

19. The orthopedic implant assembly of claim 15, wherein:

respective ones of the plurality of rings include convex-conical-frustum-shaped ring surfaces opposite the concave-conical-frustum-shaped ring surfaces;

wherein the one or more openings comprises a plurality of openings and the bone plate defines, at entry regions of respective ones of the plurality of openings thereof, respective concave-conical-frustum-shaped bone plate surfaces configured to receive corresponding ones of the convex-conical-frustum-shaped ring surfaces.

20. The orthopedic implant assembly of claim 13, wherein the piezoelectric material includes at least one of polyvinylidene fluoride or polyvinylidene difluoride (PVDF).

21. The orthopedic implant assembly of claim 13, wherein a material of the bone plate and a material of the second component is selected from the group consisting of an electrically conductive material, an electrically non-conductive material, and combinations thereof.

22. The orthopedic implant assembly of claim 13, wherein the bone plate, the first component and the second component are configured such that the bone plate and the second component are to cause at least one of a compressive force or a shear force on the first component.

23. The orthopedic implant assembly of claim 22, wherein the at least one of the compressive force or the shear force are to be distributed unevenly throughout the first component.

24. The orthopedic implant assembly of claim 13, wherein the second component has an outer surface, and wherein the first component is configured to produce an electrical output corresponding to a load applied to the outer surface of the bone plate and to the outer surface of the second component.

25. An orthopedic implant assembly comprising:

a bone plate having a distal surface configured to contact a fractured bone, a proximal surface opposite the distal surface, and a plurality of openings extending between the proximal surface and the distal surface;

a plurality of rings, each ring of the plurality of rings comprising a piezoelectric material and having a frustoconical shape and a concave-conical-frustum-shaped ring surface; and a plurality of fasteners, each fastener having a convex-conical-frustum-shaped bearing surfaces at an underside of heads of respective ones of the plurality of fasteners, wherein the plurality of rings are configured to be disposed in the plurality of openings between the bone plate and the plurality of fasteners, with the convex-conical-frustum-shaped bearing surfaces of the plurality of fasteners deforming respective concave-conical-frustum-shaped ring surfaces to conform to the convex-conical-frustum-shaped bearing surfaces of the plurality of fasteners, while the plurality of fasteners extend through the plurality of openings to attach the orthopedic implant assembly to a bone.

* * * * *